US006818403B2

(12) United States Patent
Kirk et al.

(10) Patent No.: US 6,818,403 B2
(45) Date of Patent: Nov. 16, 2004

(54) METHOD OF MONITORING HAPTOTAXIS

(75) Inventors: Gregory L. Kirk, Winchester, MA (US); Matthew Brown, Brighton, MA (US); Emanuele Ostuni, Watertown, MA (US); Enoch Kim, Boston, MA (US); Bernardo D. Aumond, Somerville, MA (US); Olivier Schueller, Somerville, MA (US); Paul Sweetnam, Marblehead, MA (US); Brian Benoit, Westborough, MA (US)

(73) Assignee: Surface Logix, Inc., Brighton, MA (US)

( * ) Notice: Subject to any disclaimer, the term of this patent is extended or adjusted under 35 U.S.C. 154(b) by 236 days.

(21) Appl. No.: 10/097,304

(22) Filed: Mar. 15, 2002

(65) Prior Publication Data

US 2003/0022153 A1 Jan. 30, 2003

Related U.S. Application Data

(63) Continuation-in-part of application No. 09/709,776, filed on Nov. 8, 2000.
(60) Provisional application No. 60/363,355, filed on Mar. 12, 2002, provisional application No. 60/334,548, filed on Dec. 3, 2001, provisional application No. 60/330,456, filed on Oct. 22, 2001, provisional application No. 60/328,103, filed on Oct. 11, 2001, provisional application No. 60/323,742, filed on Sep. 21, 2001, provisional application No. 60/312,405, filed on Aug. 15, 2001, and provisional application No. 60/307,886, filed on Jul. 27, 2001.

(51) Int. Cl.[7] .................................................. C12Q 1/68
(52) U.S. Cl. .............................. 435/6; 435/29; 435/177
(58) Field of Search .............................. 435/6, 29, 177, 435/288.4, 288.5, 288.6

(56) References Cited

U.S. PATENT DOCUMENTS

| 5,284,753 A | 2/1994 | Goodwin, Jr. ............... 435/288 |
| 5,302,515 A | 4/1994 | Goodwin, Jr. ................ 435/29 |
| 5,422,270 A | 6/1995 | Caspi ......................... 435/288 |
| 5,514,555 A | 5/1996 | Springer et al. |
| 5,601,997 A | 2/1997 | Tchao .......................... 435/29 |
| 5,744,366 A | 4/1998 | Kricka et al. ................ 422/101 |
| 5,763,194 A | 6/1998 | Slowiaczek et al. ......... 435/7.2 |
| 5,935,850 A | 8/1999 | Clark et al. ................... 435/325 |
| 5,962,250 A | 10/1999 | Gavin et al. .................... 435/29 |
| 6,027,873 A | 2/2000 | Schellenberger et al. |
| 6,238,874 B1 | 5/2001 | Jarnagin et al. .............. 435/7.2 |
| 6,321,791 B1 | 11/2001 | Chow .......................... 137/833 |
| 6,329,201 B1 | 12/2001 | Wagner et al. ............... 435/320 |
| 6,558,904 B2 | 5/2003 | Ermantraut et al. ........... 435/6 |

FOREIGN PATENT DOCUMENTS

| WO | WO 98/07069 | 2/1998 |
| WO | WO 00/07007 | 2/2000 |
| WO | WO 01/32827 A1 | 5/2001 |
| WO | WO 01/34302 A2 | 5/2001 |
| WO | WO 01/69240 A1 | 9/2001 |
| WO | WO 01/70389 A2 | 9/2001 |

OTHER PUBLICATIONS

"Formation of Gradients of Proteins on Surfaces with Microfluidic Networks", Caelen et al.: Langmuir (2000) vol. 16, pp. 9125–9130.
"Gradient Micropattern Immobilization of BGF to Investigate the Effect of Artificial Juxtacrine Stimulation", Chen et al.: Biomaterials (2001) pp. 2453–2457.
"How to Prepare Tunable Planar Molecular Chemical Gradients", Kirill Efimenko and Jan Genzer: Advanced Materials (2001) vol. 13, No. 20, pp. 1560–1563.
"Electroosmotic Properties of Microfluidic Channels Composed of Poly (Dimethylsiloxane)", Ren et al.: Journal of Chromatography B, (2001) vol. 762, pp. 117–125.
"A Firin or Collagen Gel Assay for Tissue Cell Chemotaxis: Assessment of Fibroblast Chemotaxis to GRGDSP", Knapp et al.:Experimental Cell Research, (1999) vol. 247, pp. 543–553.
"Development and Characterization of an ELISA assay in PDMS Microfluidic Channels", Eteshola et al.:Sensors and Actuators (2001), vol. B72/2, pp. 129–133.
"Rapid and quantitative in vitro measurement of cellular chemotaxis and invasion", Penno et al: Methods in Cell Science (1997) vol. 19, pp. 189–195.
"Hydrodynamic Effects on Microcapillary Motility and Chemotaxis Assays of *Methylosinus trichosporium* OB3b", Shonnard et al.: Applied and Envrionmental Microbiology, (1992) vol. 58, No. 9, pp. 2737–2743.
"Effect of Cryopreservation on Chemotaxis of Lynphocytes" Abda et al.: Cryobiology (1998) vol. 36, pp. 184–193.
"Automated Real–Time Measurement of Chemotactic Cell Motility" Hadjout et al.: BioTechniques (2001) vol. 31, pp. 1130–1138.
"Transmembrane Motibility Assay of Transiently Transfected Cells by Fluorescent Cell Counting and Luciferase Measurement" C. Battaglia et al., BioTechniques (2000) vol. 29, pp. 81–86.

(List continued on next page.)

Primary Examiner—David A. Redding
(74) Attorney, Agent, or Firm—Kenyon & Kenyon

(57) ABSTRACT

The present invention discloses a method of monitoring haptotaxis comprising: providing a device for monitoring haptotaxis having a housing defining a chamber. The chamber includes: a first well region including at least one first well, the first well region configured to receive a test agent therein and further including biomolecules immobilized therein; a second well region including at least one second well, the second well region configured to receive a sample comprising cells therein and further being horizontally offset with respect to the first well region in a test orientation of the device; and a channel region with biomolecules immobilized therein and including at least one channel connecting the first well region and the second well region with one another. The method also includes forming a surface concentration gradient along a longitudinal axis of the chamber by decreasing the concentration of biomolecules from the at least one first well to the at least one second well; placing a first sample comprising cells in the at least one second well; and monitoring haptotaxis of the cells.

15 Claims, 17 Drawing Sheets

OTHER PUBLICATIONS

"Experimental/Molecular Therapeutics 27" Proceedings of the American Association for Cancer Research (2001) vol. 42, p. 484.

"Motility and chemotaxis in *Serpulina hyodysenteriae*" Kennedy et al: Veterinary Microbiology (1996) vol. 49, pp. 21–30.

"Tumor necrosis factor–alpha decreases neutrophil chemotaxis to N–formyl–1–methionyl–1–leucy–1–phenylalanine: analysis of single cell movement." Vollmer et al.: Journal of Leukocyte Biology (1992) vol. 52, No. 6, pp. 630–636.

"Endothelial Cell Migration and Invasiveness Are Induced by a Soluble Factor Produced by Murine Endothelioma Cells Transformed by Polyuoma Virus Middle T. Oncogene" Taraboletti et al.: Cancer Research (1993) vol. 53, pp. 3812–3816.

"Measurement of Leukocyte Motility and Chemotaxis Parameters with a Linear Under–Agarose Migration Assay" D. Lauffenburger et al.: The Journal of Immunology (1983) vol. 131, No. 2, pp. 940–947.

"Micropatterned solid–supported membranes formed by micromolding in capillaries" Andreas Janshoff et al.: Eur Biophys J. (2000) vol. 29, pp. 549–554.

"Influence of Technical Parameters on the in Vitro Motility of Equine Neutrophils in the Presence of *Streptococcal* Culture Supernatant" Blancquaert et al.: Veterinary Immunology and Immunopathology, (1989) vol. 23, pp. 85–101.

"Cell Movement Analysis in a Necrotactic Assay" Gruler: Blood Cells (1984) vol. 10, pp. 107–121.

METHOD OF MONITORING HAPTOTAXIS

RELATED APPLICATIONS

This application is a continuation-in-part application of U.S. application Ser. No. 09/709,776, filed on Nov. 8, 2000 and claims the benefit of U.S. Provisional Application No. 60/307,886, filed on Jul. 27, 2001; U.S. Provisional Application No. 60/312,405, filed on Aug. 15, 2001; U.S. Provisional Application No. 60/323,742, filed on Sep. 21, 2001; U.S. Provisional Application No. 60/328,103, filed on Oct. 11, 2001; U.S. Provisional Application No. 60/330,456, filed on Oct. 22, 2001; U.S. Provisional Application No. 60/334,548, filed Dec. 3, 2001; and U.S Provisional Application No. 60/363,355, filed on Mar. 12, 2002, all of which are herein incorporated by reference in their entirety.

FIELD OF THE INVENTION

The present invention relates generally to a method of monitoring haptotaxis.

BACKGROUND

Test devices, such as those used in chemotaxis, haptotaxis and chemoinvasion are well known. Such devices are disclosed for example in U.S. Pat. Nos. 6,329,164, 6,238,874, and 5,302,515.

Three processes involved in cell migration are chemotaxis, haptotaxis, and chemoinvasion. Chemotaxis is defined as the movement of cells induced by a concentration gradient of a soluble chemotactic stimulus. Haptotaxis is defined as the movement of cells in response to a concentration gradient of a substrate-bound stimulus. Chemoinvasion is defined as the movement of cells into and/or through a barrier or gel matrix. The study of chemotaxis/haptotaxis and chemoinvasion and the effects of external stimuli on such behavior are prevalent throughout contemporary biological research. Generally, this research involves exposing a cell to external stimuli and studying the cell's reaction. By placing a living cell into various environments and exposing it to different external stimuli, both the internal workings of the cell and the effects of the external stimuli on the cell can be measured, recorded, and better understood.

A cell's migration in response to a chemical stimulus is a particularly important consideration for understanding various disease processes and accordingly developing and evaluating therapeutic candidates for these diseases. By documenting the cell migration of a cell or a group of cells in response to a chemical stimulus, such as a therapeutic agent, the effectiveness of the chemical stimulus can be better understood. Typically, studies of disease processes in various medical fields, such as oncology, immunology, angiogenesis, wound healing, and neurobiology involve analyzing the chemotactic and invasive properties of living cells. For example, in the field of oncology, cell migration is an important consideration in understanding the process of metastasis. During metastasis, cancer cells of a typical solid tumor must loosen their adhesion to neighboring cells, escape from the tissue of origin, invade other tissues by degrading the tissues' extracellular matrix until reaching a blood or lymphatic vessel, cross the basal lamina and endothelial lining of the vessel to enter circulation, exit from circulation elsewhere in the body, and survive and proliferate in the new environment in which they ultimately reside. Therefore, studying the cancer cells' migration may aid in understanding the process of metastasis and developing therapeutic agents that potentially inhibit this process. In the inflammatory disease field, cell migration is also an important consideration in understanding the inflammatory response. During the inflammation response, leukocytes migrate to the damaged tissue area and assist in fighting the infection or healing the wound. The leukocytes migrate through the capillary adhering to the endothelial cells lining the capillary. The leukocytes then squeeze between the endothelial cells and use digestive enzymes to crawl across the basal lamina. Therefore, studying the leukocytes migrating across the endothelial cells and invading the basal lamina may aid in understanding the inflammation process and developing therapeutic agents that inhibit this process in inflammatory diseases such as adult respiratory distress sydrome (ARDS), rheumotoid arthritis, and inflammatory skin diseases. Cell migration is also an important consideration in the field of angiogenesis. When a capillary sprouts from an existing small vessel, an endothelial cell initially extends from the wall of the existing small vessel generating a new capillary branch and pseudopodia guide the growth of the capillary sprout into the surrounding connective tissue. New growth of these capillaries enables cancerous growths to enlarge and spread and contributes, for example, to the blindness that can accompany diabetes. Conversely, lack of capillary production can contribute to tissue death in cardiac muscle after, for example, a heart attack. Therefore studying the migration of endothelial cells as new capillaries form from existing capillaries may aid in understanding angiogenesis and optimizing drugs that block vessel growth or improve vessel function. In addition, studying cell migration can also provide insight into the processes of tissue regeneration, organ transplantation, autoimmune diseases, and many other degenerative diseases and conditions.

Cell migration assays are often used in conducting these types of research. Commercially available devices for creating such assays are sometimes based on or employ a transwell system (a vessel partitioned by a thin porous membrane to form an upper compartment and a lower compartment). To study cell chemotaxis, cells are placed in the upper compartment and a migratory stimulus is placed in the lower compartment. After a sufficient incubation period, the cells are fixed, stained, and counted to study the effects of the stimulus on cell chemotaxis across the membrane.

To study chemoinvasion, a uniform layer of a MATRIGEL™ matrix is placed over the membrane to occlude the pores of the membrane. Cells are seeded onto the MATRIGEL™ matrix in the upper compartment and a chemoattractant is placed in the lower compartment. Invasive cells attach to and invade the matrix passing through the porous membrane. Non-invasive cells do not migrate through the occluded pores. After a sufficient incubation period, the cells may be fixed, stained, and counted to study the effects of the stimulus on cell invasion across the membrane.

The use of transwells has several shortcomings. Assays employing transwells require a labor-intensive protocol that is not readily adaptable to high-throughput screening and processing. Because of the configuration of a transwell system, it is difficult to integrate with existing robotic liquid handling systems and automatic image acquisition systems. Therefore, much of the screening and processing, such as counting cells, is done manually which is a time-consuming, tedious, and expensive process. Cell counting is also subjective and often involves statistical approximations. Specifically, due to the time and expense associated with examining an entire filter, only randomly selected representative areas may be counted. Moreover, even when these areas are counted, a technician must exercise his or her judgment when accounting for a cell that has only partially migrated through the filter.

Transwell-based assays have intrinsic limitations imposed by the thin membranes utilized in transwell systems. The membrane is only 50–30 microns ($\mu$m) thick, and a chemical concentration gradient that forms across the membrane is transient and lasts for a short period. If a cell chemotaxis assay requires the chemotactic gradient to be generated over a long distance (>100–200 $\mu$m) and to be stable over at least two hours, currently available transwell assays cannot be satisfactorily performed.

Notwithstanding the above, perhaps the most significant disadvantage of transwells is the lack of real-time observation of chemotaxis and chemoinvasion. In particular, the changes in cell morphology during chemotaxis cannot be observed in real-time with the use of transwells. In transwells, when the cells are fixed to a slide, as required for observation, they are killed. Consequently, once a cell is observed it can no longer be reintroduced into the assay or studied at subsequent periods of exposure to a test agent. Therefore, in order to study the progress of a cell and the changes in a cell's morphology in response to a test agent, it is necessary to run concurrent samples that may be slated for observation at various time periods before and after the introduction of the test agent. In light of the multiple samples required for each test, in addition to the positive and negative controls required to obtain reliable data, a single chemotaxis assay can require dozens of filters, each of which needs to be individually examined and counted-an onerous and time-consuming task.

More recently, devices for measuring chemotaxis and chemoinvasion have become available which employ a configuration in which two wells are horizontally offset with respect to one another. This configuration of a device was introduced by Sally Zigmond in 1977 and, hereafter referred to as the "Zigmond device," consists of a 25 millimeters (mm)×75 mm glass slide with two grooves 4 mm wide and 1 mm deep, separated by a 1 mm bridge. One of the grooves is filled with an attractant and the other groove is filled with a control solution, thus forming a concentration gradient across the bridge. Cells are then added to the other groove. Two holes are provided at each end of the slide to accept pin clamps. The clamps hold a cover glass in place during incubation and observation of the cells. Because of the size and configuration of the Zigmond chamber, it does not allow integration with existing robotic liquid handling systems and automatic image acquisition systems. Further, as with transwell-based systems, the changes in cell morphology during chemotaxis cannot be observed in real-time with the use of the Zigmond chamber as the cells are fixed to a slide for observation. In addition, the pin clamps must be assembled with an allen wrench and thus the device requires extra handling, positioning, and alignment before performing the assay. Such handling and positioning of the cover glass on the glass slide, as well as the rigidity of the cover glass, can potentially damage or interfere any surface treatment on the bridge.

A chemotaxis device attempting to solve the problem of lack of real-time observation is the "Dunn chamber." The Dunn chamber consists of a specially constructed microslide with a central circular sink and a concentric annular moat. In an assay using a Dunn chamber, cells migrate on a coverslip, which is placed inverted on the Dunn chamber, towards a chemotactic stimulus. The cells are monitored over-night using a phase-contrast microscope fitted with a video camera connected to a computer with an image-grabber board. In addition to the problems of rigidity of the coverslip and the lack of integration int o existing robotic liquid handling systems, a major problem with the Dunn chamber assay is that only a very small number of cells are monitored (typically ten). The average behavior of this very small sample may not be typical of the population as a whole. A second major problem is that replication is very restricted. Each control chamber and each treatment chamber must be viewed in separate microscopes, each one similarly equipped with camera and computer.

Another chemotaxis device known in the art is disclosed in U.S. Pat. No. 6,238,874 to Jarnigan et. al. (the '874 patent). The '874 patent discloses various embodiments of test devices that may be used to monitor chemotaxis. However, disadvantageously, the devices in Jamagin et al. can not be easily sealed or assembled or peeled and disassembled. Thus, it is difficult to maintain surfaces that are prepared chemically or biologically during assembly. The test devices of the '874 patent are therefore more suited for one-time use. Also, disassembly and collection of cells is difficult to do without damage to the cells or without disturbing the cell positions.

The prior art has failed to provide a test device, such as a device for monitoring chemotaxis, haptotaxis, and/or chemoinvasion, which device is easily assembled and dissembled. In addition, the prior art has failed to provide a test device for monitoring chemotaxis and/or chemoinvasion, which is not limited to measuring the effects on cell migration of chemoattractants, chemorepellants and chemostimulants.

SUMMARY OF THE INVENTION

The present invention provide a method of monitoring haptotaxis. The method includes providing a device for monitoring haptotaxis having a housing defining a chamber. The chamber includes a first well region including at least one first well, the first well region configured to receive a test agent therein and further including biomolecules immobilized therein; a second well region including at least one second well, the second well region configured to receive a sample comprising cells therein and further being horizontally offset with respect to the first well region in a test orientation of the device; and a channel region with biomolecules immobilized therein and including at least one channel connecting the first well region and the second well region with one another. The method further includes forming a surface concentration gradient along a longitudinal axis of the chamber by decreasing the concentration of biomolecules from the at least one first well to the at least one second well. The method additionally includes placing a first sample comprising cells in the at least one second well. The method also includes monitoring haptotaxis of the cells.

BRIEF DESCRIPTION OF THE DRAWINGS

The various features of the invention will best be appreciated by simultaneous reference to the description that follows and the accompanying drawings, in which.

DETAILED DESCRIPTION OF THE EMBODIMENTS

Figure 1A:
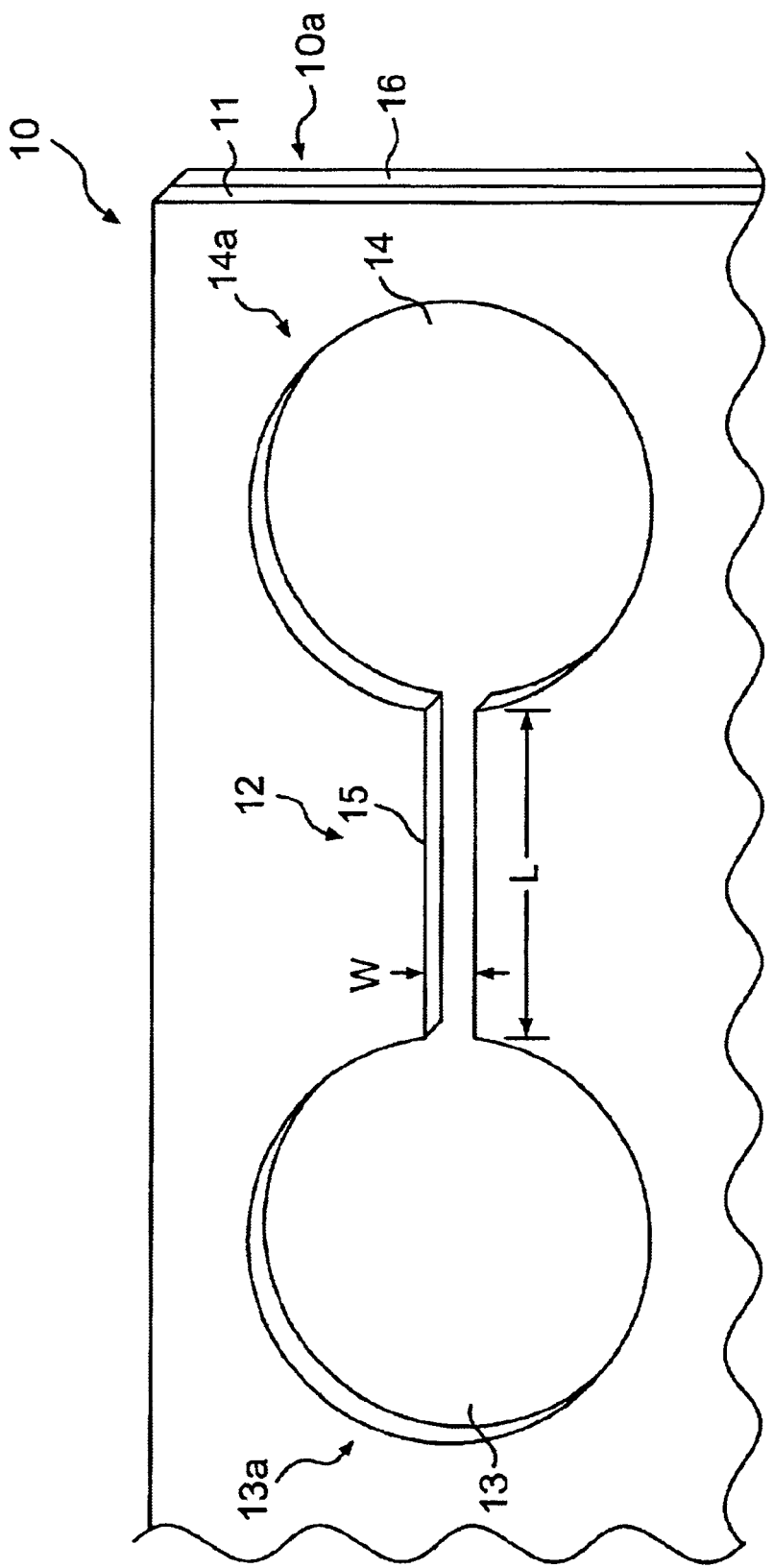
FIG. 1A is a top, perspective view, in partial cross section, of a portion of an embodiment of test device according to the present invention.
Figure 1B:
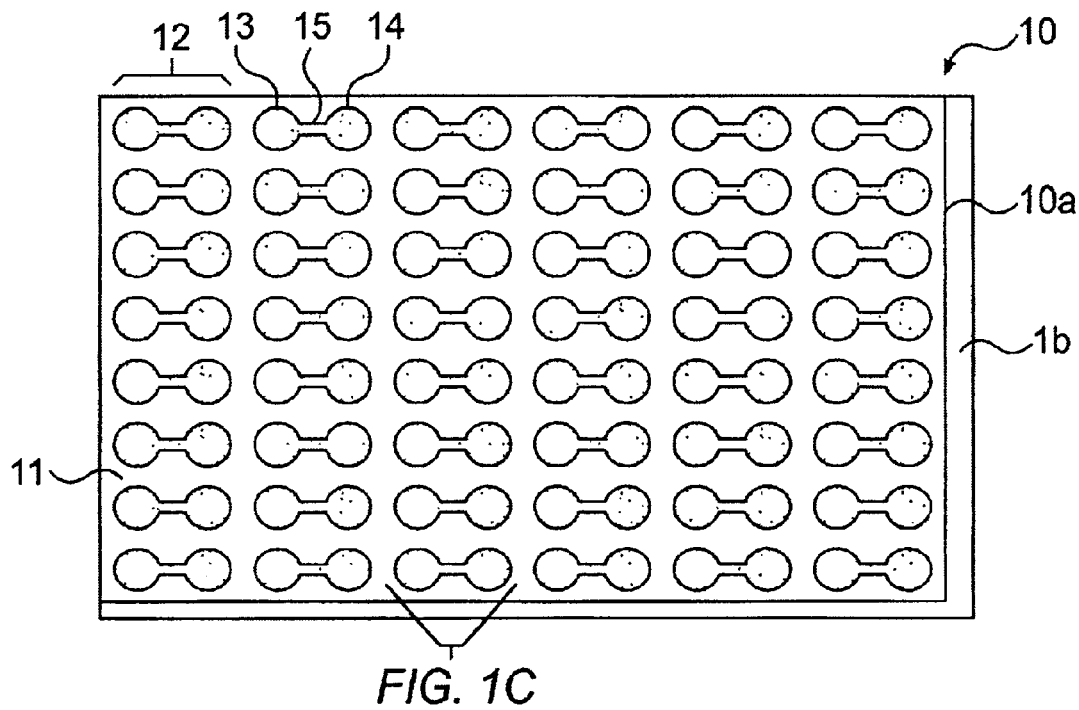
FIG. 1B is a top, perspective view of an embodiment of a test device of the present invention.
Figure 1C:
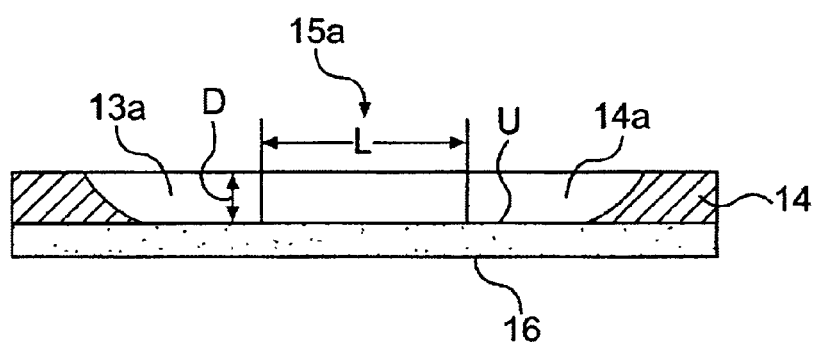
FIG. 1C is a side-elevational view of a longitudinal cross section of one of the chambers of the test device of FIG. 1B.

As shown in FIG. 1A, according to one embodiment of the present invention, a test device 10, such as, for example, a cellular chemotaxis/haptotaxis and/or chemoinvasion device, includes a housing 10a comprising a support member 16 and a top member 11 mounted to the support member 16 by being placed in substantially fluid-tight, conformal contact with the support member 16. In the context of the present invention, "conformal contact" means substantially form-fitting, substantially fluid-tight contact. The support member 16 and the top member 11 are configured such that they together define a discrete chamber 12 as shown. Preferably test device 10 comprises a plurality of discrete chambers, as shown by way of example in the embodiment of FIG. 1B. The discrete chamber 12 includes a first well region 13a including at least one first well 13 and second well region 14a including at least one second well 14, the second well region further being horizontally offset with respect to the first well region in a test orientation of the device. The "test orientation" of the device is meant to refer to a spatial orientation of the device during testing. As shown in FIG. 1C, device 10 further includes a channel region 15a including at least one channel 15 connecting the first well region 13a and the second well region 14a with one another. In the embodiments of FIGS. 1A–2C, each well region includes a single well, and the channel region includes a single channel. As seen in FIG. 1C, each well is defined by a through-hole in top member 11, corresponding to well 13 and well 14 respectively, and by an upper surface U of support member 16. In particular, the sides of each well 13 and 14 are defined by the walls of the through holes in the top member 11, and the bottoms of well 13 and 14 are defined by the upper surface U of support member 16. It is noted that in the context of the present invention, "top," "bottom," "upper" and "side" are defined relative to the test orientation of the device. As seen collectively in FIGS. 1A and 1C, a length L of channel region 15a is defined in a direction of the longitudinal axis of channel region 15a; a depth D of channel region 15a is defined in a direction normal to upper surface U of support member 16; a width W is defined in a direction normal to the length L and depth D of channel region 15a. According to one embodiment of the present invention, the chamber's first well 13 is adapted to receive a test agent, a soluble test substance and/or a test agent comprising immobilized biomolecules, which potentially affects chemotaxis or haptotaxis. Biomolecules include, but not limited to, DNA, RNA, proteins, peptides, carbohydrates, cells, chemicals, biochemicals, and small molecules. The chamber's second well 14 is adapted to receive a biological sample of cells. Immobilized biomolecules are biomolecules that are attracted to support member 16 with an attractive force stronger than the attractive forces that are present in the environment surrounding the support member, such as solvating and turbulent forces present in a fluid medium. Non-limiting examples of the test agent include chemorepellants, chemotactic inhibitors, and chemoattractants, such as growth factors, cytokines, chemokines, nutrients, small molecules, and peptides. Alternatively, the chamber's first well 13 is adapted to receive a biological sample of cells and the chamber's second well 14 is adapted to receive a test agent.

In one embodiment of the present invention, when a soluble test substance is used as the test agent, channel region 15a preferably contains a gel matrix. The gel matrix allows the formation of a solution concentration gradient from first well region 13a towards second well region 14a as the solute diffuses from an area of higher concentration (well region 13a) through a semi-permeable matrix (the gel matrix) to an area of lower concentration (well region 14a). If the soluble test substance comprises a chemoattractant, in order for the cells to migrate through the matrix in the direction of the solution concentration gradient towards well region 13a, the cells must degrade this matrix by releasing enzymes such as matrix metalloproteases. This cell chemotaxis and invasion may be subsequently observed, measured, and recorded.

In one embodiment of the present invention, utilizing immobilized biomolecules as the test agent, the biomolecules are preferably immobilized or bound on the portion of support member 16 underlying channel region 15a and underlying through hole for well region 13a. The concentration of biomolecules decreases along the longitudinal axis of the device from well region 13a towards well region 14a forming a surface concentration gradient of immobilized biomolecules and the biological sample of cells potentially responds to this surface gradient. This cell haptotaxis may be subsequently observed, measured, and recorded.

With respect to particular specifications of device 10, top member 11 is made of a material that is adapted to effect conformal contact, preferably reversible conformal contact, with support member 16. According to embodiments of the present invention, the flexibility of such a material, among other things, allows the top member to form-fittingly adhere to the upper surface U of support member 16 in such a way as to form a substantially fluid-tight seal therewith. The conformal contact should preferably be strong enough to prevent slippage of the top member on the support member surface. Where the conformal contact is reversible, the top member may be made of a material having the structural integrity to allow the top member to be removed by a simple peeling process. This would allow top member 11 to be removed and cells at certain positions collected. Preferably, the peeling process does not disturb any surface treatment or cell positions of support member 16. Physical striations, pockets, SAMs, gels, peptides, antibodies, or carbohydrates can be placed on support member 16 and the top member 11 subsequently can be placed over support member 16 without any damage to these structures. Additionally, the substantially fluid-tight seal effected between top member 11 and support member 16 by virtue of the conformal contact of top member 11 with support member 16 prevents fluid from leaking from one chamber to an adjacent chamber, and also prevents contaminants from entering the wells. The seal preferably occurs essentially instantaneously without the necessity to maintain external pressure. The conformal contact obviates the need to use a sealing agent to seal top member 11 to support member 16. Although embodiments of the present invention encompass use of a sealing agent, the fact that such a use is obviated according to a preferred embodiment provides a cost-saving, time-saving alternative, and further eliminates a risk of contamination of each chamber 12 by a sealing agent. Preferably, the top member 11 is made of a material that does not degrade and is not easily damaged by virtue of being used in multiple tests, and that affords considerable variability in the top member's configuration during manufacture of the same. More preferably, the material may be selected for allowing the top member to be made using photolithography. In a preferred embodiment, the material comprises an elastomer such as silicone, natural or synthetic rubber, or polyurethane. In a more preferred embodiment, the material is polydimethylsiloxane ("PDMS").

According to a preferred embodiment of a method of the present invention, standard photolithographic procedures can be used to produce a silicon master that is the negative image of any desired configuration of top member 11. For example, the dimensions of chambers 12, such as the size of well regions 13a and 14a, or the length of channel region 15a, can be altered to fit any advantageous specification. Once a suitable design for the master is chosen and the master is fabricated according to such a design, the material is either spin cast, injected, or poured over the master and cured. Once the mold is created, this process may be repeated as often as necessary. This process not only provides great flexibility in the top member's design, it also allows the top members to be massively replicated. The present invention also contemplates different methods of fabricating device 10 including, for example, e-beam lithography, laser-assisted etching, and transfer printing.

Device 10 preferably fits in the footprint of an industry standard microtiter plate. As such, device 10 preferably has the same outer dimensions and overall size of an industry standard microtiter plate. Additionally, when chamber 12 comprises a plurality of chambers, either the chambers 12 themselves, or the wells of each chamber 12, may have the same pitch of an industry standard microtiter plate. The term "pitch" used herein refers to the distance between respective vertical centerlines between adjacent chambers or adjacent wells in the test orientation of the device. The embodiment of device 10, shown in FIG. 1B, comprises 48 chambers designed in the format of a standard 96-well plate, with each well fitting in the space of each macrowell of the plate. The size and number of the plurality of chambers 12 can correspond to the footprint of standard 24-, 96-, 384-, 768- and 1536-well microtiter plates. For example, for a 96 well microtiter plate, device 10 may comprise 48 chambers 12 and therefore 48 experiments can be conducted, and for a 384 well microtiter plate, the device may comprise 192 chambers 12, and therefore 192 experiments can be conducted. The present invention also contemplates any other number of chambers and/or wells disposed in any suitable configuration. For example, if pitch or footprint standards change or new applications demand new dimensions, then device 10 may easily be changed to meet these new dimensions. By conforming to the exact dimension and specification of standard microtiter plates, embodiments of device 10 would advantageously fit into existing infrastructure of fluid handling, storage, registration, and detection. Embodiments of device 10, therefore, may be conducive to high throughput screening as they may allow robotic fluid handling and automated detection and data analysis. Top member 11 may additionally take on several different variations and embodiments. Depending on the test parameters, such as, for example, where chemotaxis, haptotaxis and/or chemoinvasion are to be monitored, the cell type, cell number, or distance over which chemotaxis or haptotaxis is required, chamber 12 of top member 11 may have various embodiments of which a few exemplary embodiments are discussed herein. With respect to a discrete chamber 12, the shape, dimensions, location, surface treatment, and numbers of channels in channel region 15a and the shape and number of wells 13 and 14 may vary.

Regarding the shape of channel region 15a, each channel 15 in the channel region 15a is not limited to a particular cross-sectional shape, as taken in a plane perpendicular to its longitudinal axis. For example, the cross section of any given channel 15 can be hexagonal, circular, semicircular, ellipsoidal, rectangular, square, or any other polygonal or curved shape.

Regarding the dimensions of a channel 15, the length L of a given channel 15 can vary based on various test parameters. For instance, the length L of a given channel 15 may vary in relation to the distance over which chemotaxis or haptotaxis is required to occur. For example, the length L of a given channel 15 can range from about 3 $\mu$m to about 18 mm in order to allow cells sufficient distance to travel and therefore sufficient opportunity to observe cell chemotaxis/haptotaxis and chemoinvasion. The width W and depth D of a given channel 15 may also vary as a function of various test parameters. For examples, the width W and depth D of a given channel 15 may vary, in a chemotaxis, haptotaxis and/or chemoinvasion device, depending on the size of the cell being studied and whether a gel matrix is added to the given channel 15. Generally, where the test device is a chemotaxis, haptotaxis and/or chemoinvasion device, a given channel 15's width W and depth D may be approximately in the range of the diameter of the cell being assayed. To discount random cellular movement, at least one of the depth D or width W of a given channel 15 should preferably be smaller than the diameter of the cell when no gel matrix is placed in the given channel 15 so that when the cells are activated, they can "squeeze" themselves through the given channel toward the test agent. If a given channel 15 contains a gel matrix, then, the depth D and width W of the given channel 15 may be greater than the diameter of the cell being assayed. Referring by way of example to the embodiments of FIGS. 1A–2C, if suspension cells such as leukocytes, which are about 3–12 $\mu$m in diameter, are in well 14 and channel 15 contains no gel, then the width W of channel 15 should range from about 3 microns to about 20 $\mu$m, and the depth D of channel 15 should range from about 3 microns to about 20 $\mu$m but at least either the depth D or width W of channel 15 should be smaller than the diameter of the cell. If leukocytes are in well 14 and channel 15 contains a gel matrix, then the width W of channel 15 should range from about 20 to about 100 $\mu$m and the depth D should range from about 20 $\mu$m to about 100 $\mu$m, and both the width W and depth D of channel 15 can be greater than the diameter of the cell assayed. Similarly, if adherent cells, such as endothelial cells which are 3–10 microns in diameter before adherence, are in well 14 and channel 15 contains no gel, then the width W and depth D of channel 15 can range from about 3 to about 20 $\mu$m, but at least either the width W or depth D of channel 15 should be smaller than the diameter of the cell assayed. If adherent cells are in well 14 and channel 15 contains a gel matrix then the width W and depth D of channel 15 should range from about 20 $\mu$m to about 200 $\mu$m and both the width W and depth D of channel 15 can be greater than the diameter of the cell assayed.

Figure 2A:
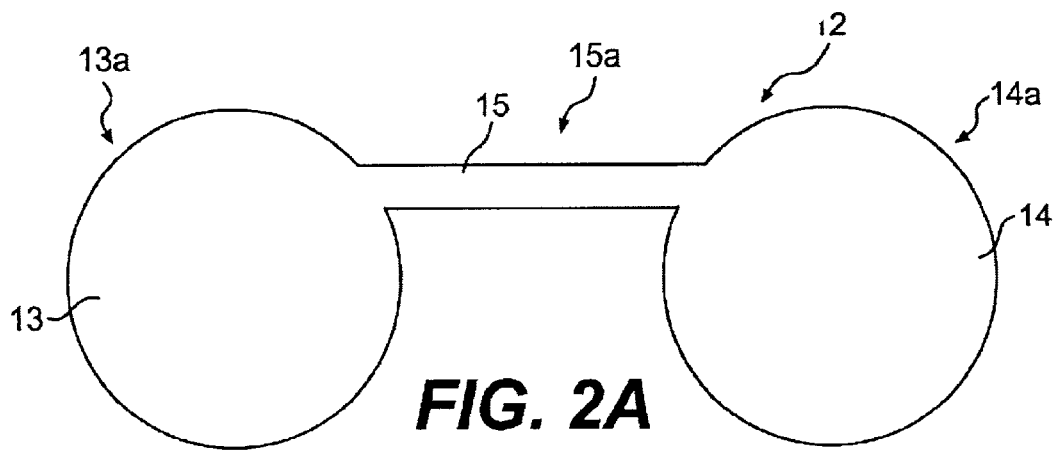
FIG. 2A is a schematic outline depicting a top plan view of an alternative embodiment of a chamber defined in a test device of the present invention, where the channel region defines a single channel.
Figure 2B:
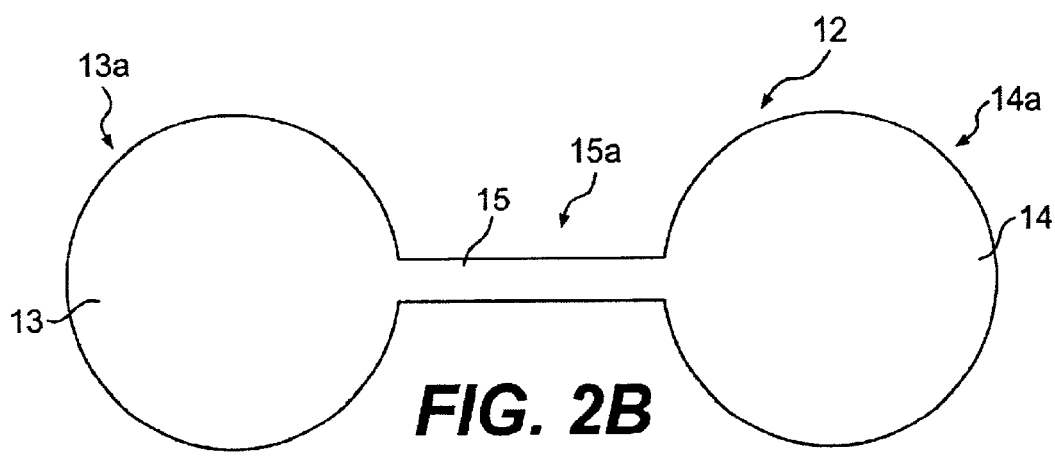
FIG. 2B is a schematic outline depicting a top plan view of the embodiment of the chambers defined in the embodiment of the test device according to FIG. 1B, where the channel region defines a single channel.
Figure 2C:
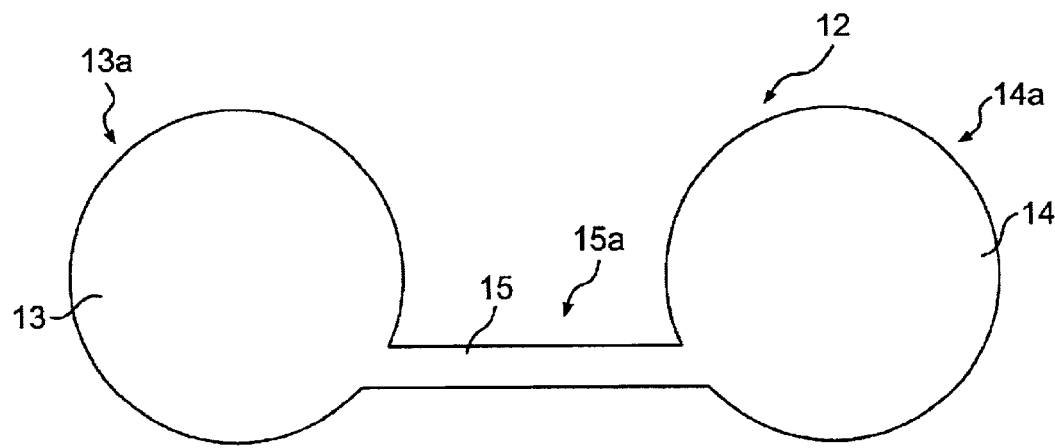
FIG. 2C is a figure similar to FIG. 2A, showing an alternative embodiment of a chamber defined in a test device of the present invention, where the channel region defines a single channel.

As seen in FIGS. 2A–2C channel 15 may connect the first well 13 to the second well 14 at respective sides of the wells, as shown in FIGS. 2A and 2C or at a central region of the wells, as shown in FIG. 2B.

Figure 3A:
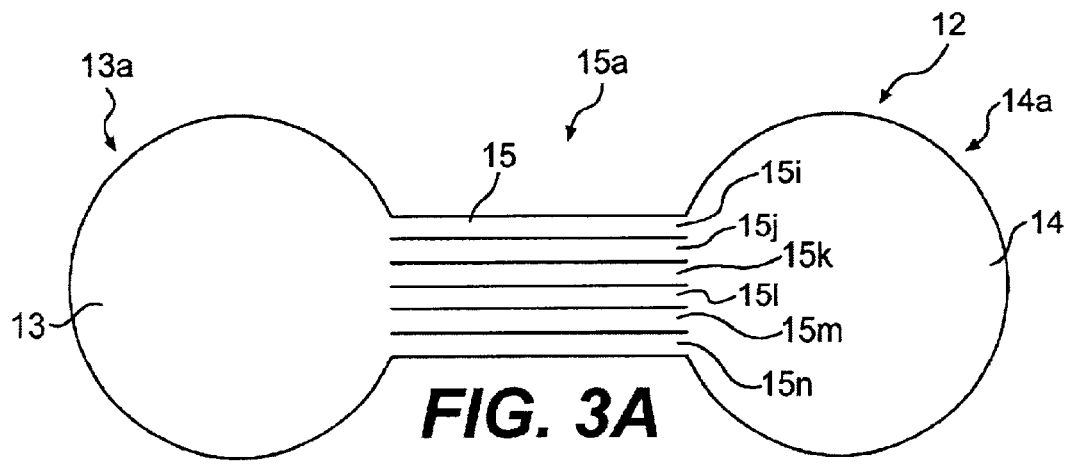
FIG. 3A is a figure similar to FIG. 2A, showing an alternative embodiment of a chamber defined in a test device of the present invention, where the channel region defines a plurality of channels having identical lengths.
Figure 3B:
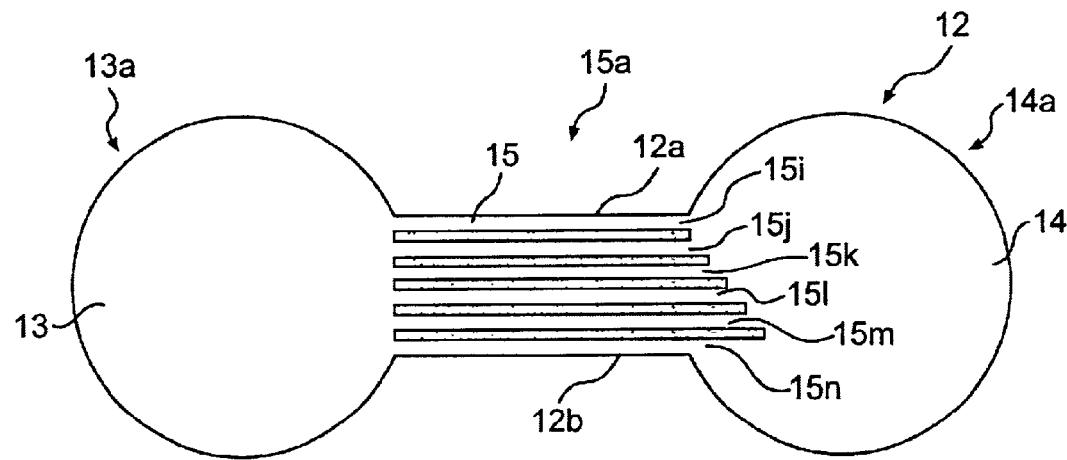
FIG. 3B is a figure similar to FIG. 3A, showing a channel region defining a plurality of channels having lengths that increase from one side of the chamber to another side of the chamber.
Figure 3C:
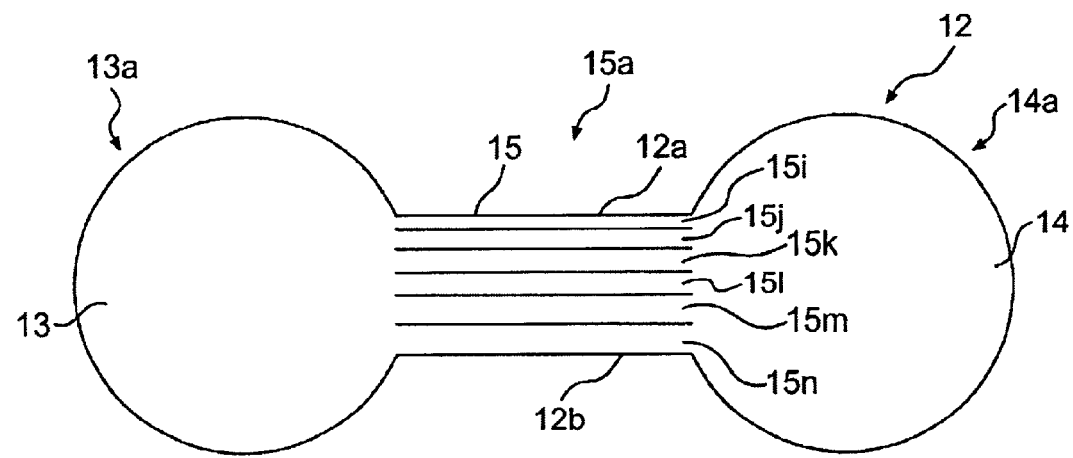
FIG. 3C is a figure similar to FIG. 3A, showing a channel region defining a plurality of channels having widths that increase from one side of the chamber to another side of the chamber.

The number of channels in channel region 15a between well regions 13a and 14a can also vary. Channel region 15a may include a plurality of channels, as shown by way of example in FIGS. 3A–3C. As seen in FIG. 3A, in a preferred configuration, the length L of each channel 15i–n between well 13 and well 14 is identical. In another embodiment as seen in FIG. 3B, the length L of each channel 15i–n of channel region 15a increases in the direction of well 14, starting from channel 15i in the side portion 12a of chamber 12 to channel 15n in the side portion 12b of chamber 12. In one embodiment, as seen in FIG. 3B, the length L of each successive channel in the plurality of channels 15 of chamber 12 increases in a direction of a width W of the channels with respect to a preceding one of the plurality of channels such that respective channel inlets at one of the first well region and the second well region, such as well region 13a as shown, are aligned along the direction of the width W of the channels. Although, in this configuration, the cells traveling in any particular channel will exit the channels and enter well 14 at points longitudinally offset with respect to one another, the section of channel region 15a closest to well region 13a is positioned so that cells ultimately entering the different channels will be aligned in a direction of the width W of the channels so that there is no longitudinal offset between them. Therefore, in comparing two adjacent channels, a first group of cells entering channel 15i has an entry position that is not longitudinally offset with respect to a second different group of cells entering channel 15j, but the first group of cells exiting channel 15i has an exit point longitudinally offset from the second group of cells exiting channel 15j. In a different embodiment of the present invention illustrated in FIG. 3C, the width W of each channel 15i–15n increases starting from channel 15i in the side portion 12a of chamber 12 to channel 15n in the side portion 12b of chamber 12. Preferably, the width W or depth D of each successive channel of the plurality of channels increases in a direction of a width W of the channels with respect to a preceding one of the plurality of channels. Alternatively, a depth D of each successive channel could increase (not shown) along a direction of the width W of the channels. It is understood to those skilled in the art, that various embodiments altering the dimensions of the channels in the channel region 15a are within the scope of the present invention. For example, the length of the channels 15i–15n need not increase in a continuous manner from channel 15i to 15n as illustrated in FIG. 3B. Instead, channel 15i–15n may have varying lengths following no particular order or pattern.

Figure 4A:
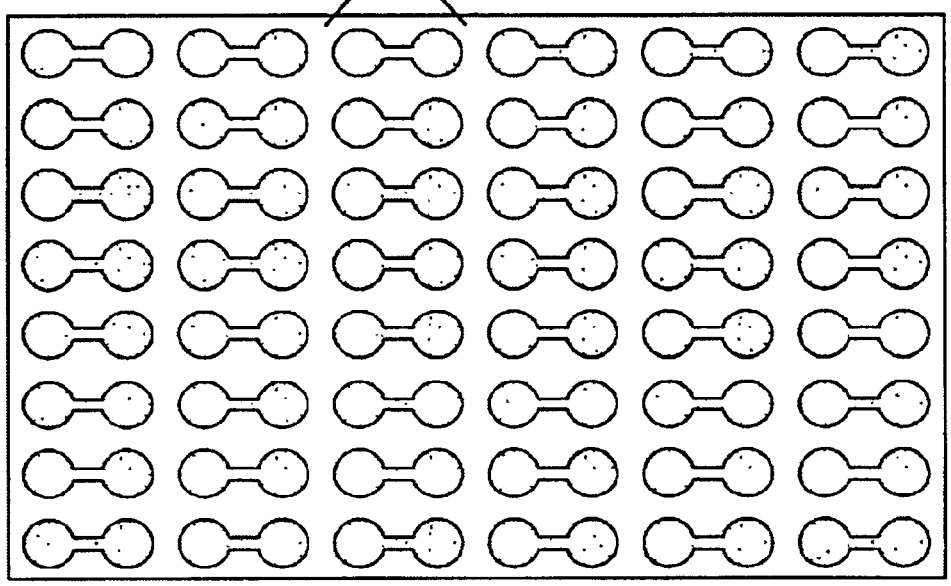
FIG. 4A is a figure similar to FIG. 1B showing an alternative embodiment of a test device according to the present invention.
Figure 4B:
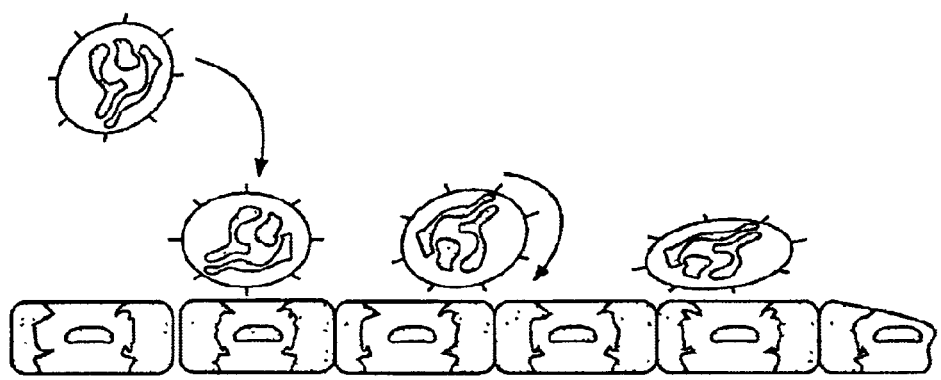
FIG. 4B is an enlarged, schematic, top plan view of a channel of FIG. 4A showing cells on the sides of the channel.

With respect to surface treatment of a given channel 15, to simulate in vivo conditions where cells are surrounded by other cells, the lateral walls of a given channel 15 may be coated with cells, such as endothelial cells 40 as seen in FIG. 4B. Non-limiting examples of endothelial cells include human umbilical vein endothelial cells or high endothelial venule cells. In another embodiment, a given channel 15 is filled with a gel matrix such as gelatin, agarose, collagen, fibrin, any natural or synthetic extracellular proteinous matrix or basal membrane mimic including, but not limited to MATRIGEL™ (Becton Dickenson Labware), or ECM GEL, (Sigma, St. Louis, Mo.), or other hydrogels containing certain factors such as cytokines, growth factors, antibodies, ligands for cell surface receptors, or chemokines. Preferably, the gel has a substantially high water content and is porous enough to allow cell chemotaxis and invasion. As mentioned above, when the test agent comprising a soluble test substance is placed in well 13, the gel facilitates formation of a solution concentration gradient along the longitudinal axis of chamber 12. Additionally, adding a gel matrix to a given channel 15 simulates the natural environment in the body, as enzyme degradation through extracellular matrix is a crucial step in the invasive process.

Figure 5:
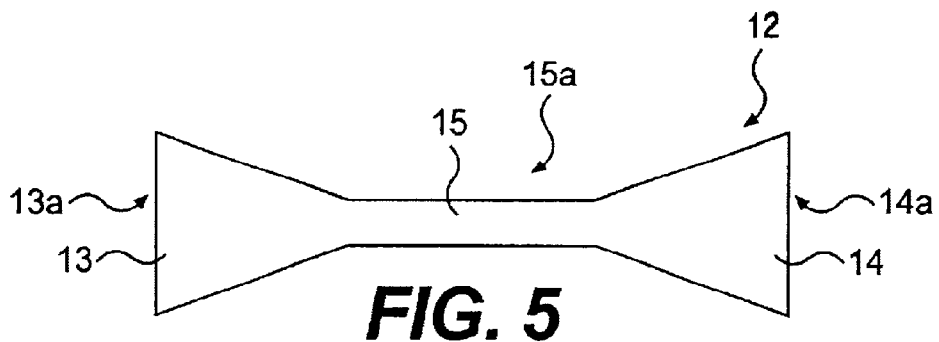
FIGS. 5 and 6 are views similar to FIG. 2A, showing an alternative embodiment of a chamber defined in a test device of the present invention, where the wells are trapezoidal in a top plan view thereof.
Figure 6:
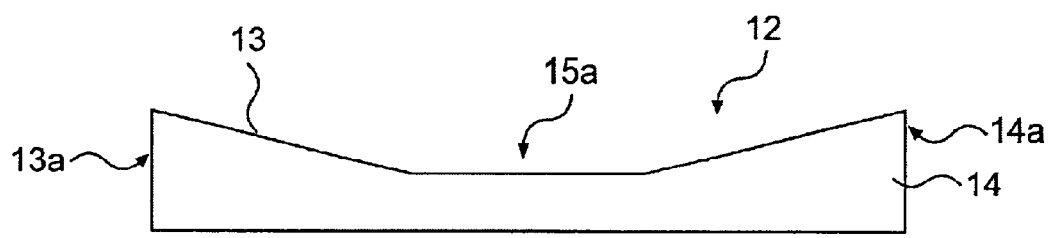
Figure 7:
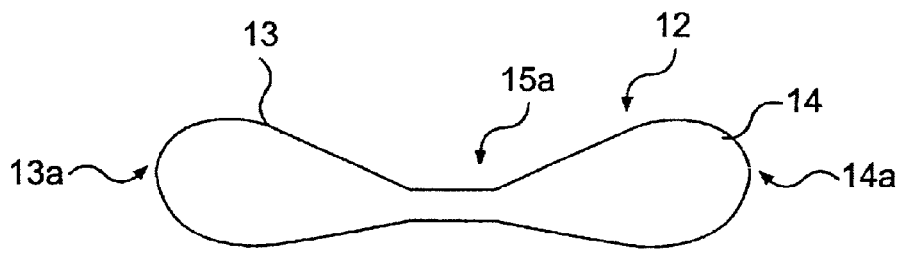
FIG. 7 is a view similar to FIG. 2A, showing an alternative embodiment of a chamber defined in a test device of the present invention, where the chamber is in the form of a FIG. 8 in a top plan view thereof.
Figure 8:
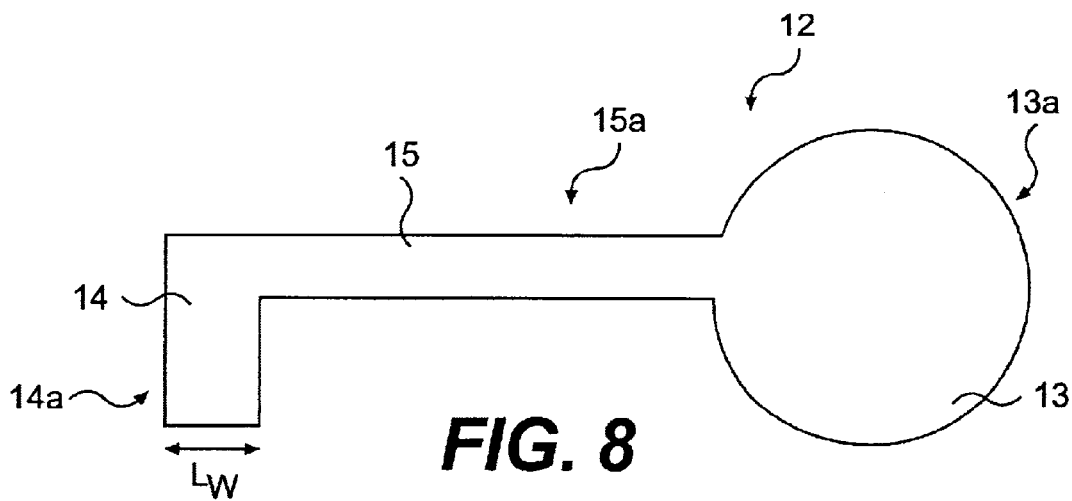
FIG. 8 is a view similar to FIG. 2A, showing an alternative embodiment of a chamber defined in a test device of the present invention, where one well is rectangular and the other well circular in a top plan view of the device.

According to the present invention, the individual wells of each well region 13a or 14a may have any shape and size. For example, the top plan contour of a given well may be circular, as shown in FIGS. 1A–2C, or trapezoidal as shown in FIGS. 5 and 6. Alternatively, the top plan contour of a given chamber may be generally in the shape of a "figure 8" as shown in FIG. 7. Preferably when using a soluble test substance as the test agent, the shape of well 13 is such that soluble test substance is readily able to access the channel 15 and thereby form the necessary solution concentration gradient along the length L of channel 15. Preferably, the shape of well 14 is such that cells are not deferred, detained, or hindered from migrating out of the first well 14, for example, by accumulating in a corner, side or other dead space of well 14. Although possible accumulation of cells in a dead space of well 14 is not restricted to any particular cell number, there exists a greater likelihood of cells accumulating in a corner of well 14 if a large number of cells are used. Therefore to maximize accessibility to the concentration gradient and to minimize the "wasting" of cells when a large cell sample is utilized, it is important that the shape of well 14 be such that a sufficiently high percentage of cells, particularly the cells in the area of well 14 furthest from channel 15, are capable of migrating out of well 14. In a different embodiment that also addresses the problem of the wasting of cells, well 14 may be shaped such that all cells have a higher probability of accessing the concentration gradient. For example as seen in FIG. 8, the length $L_w$ of well 14 in a top plan view thereof is minimized to decrease the surface area of the well. As such, the cells are closer to the concentration gradient formed in channel 15. In a preferred embodiment, the $L_w$ of well 14 in a top plan view thereof is about 1 mm to about 2 mm.

Figure 9:
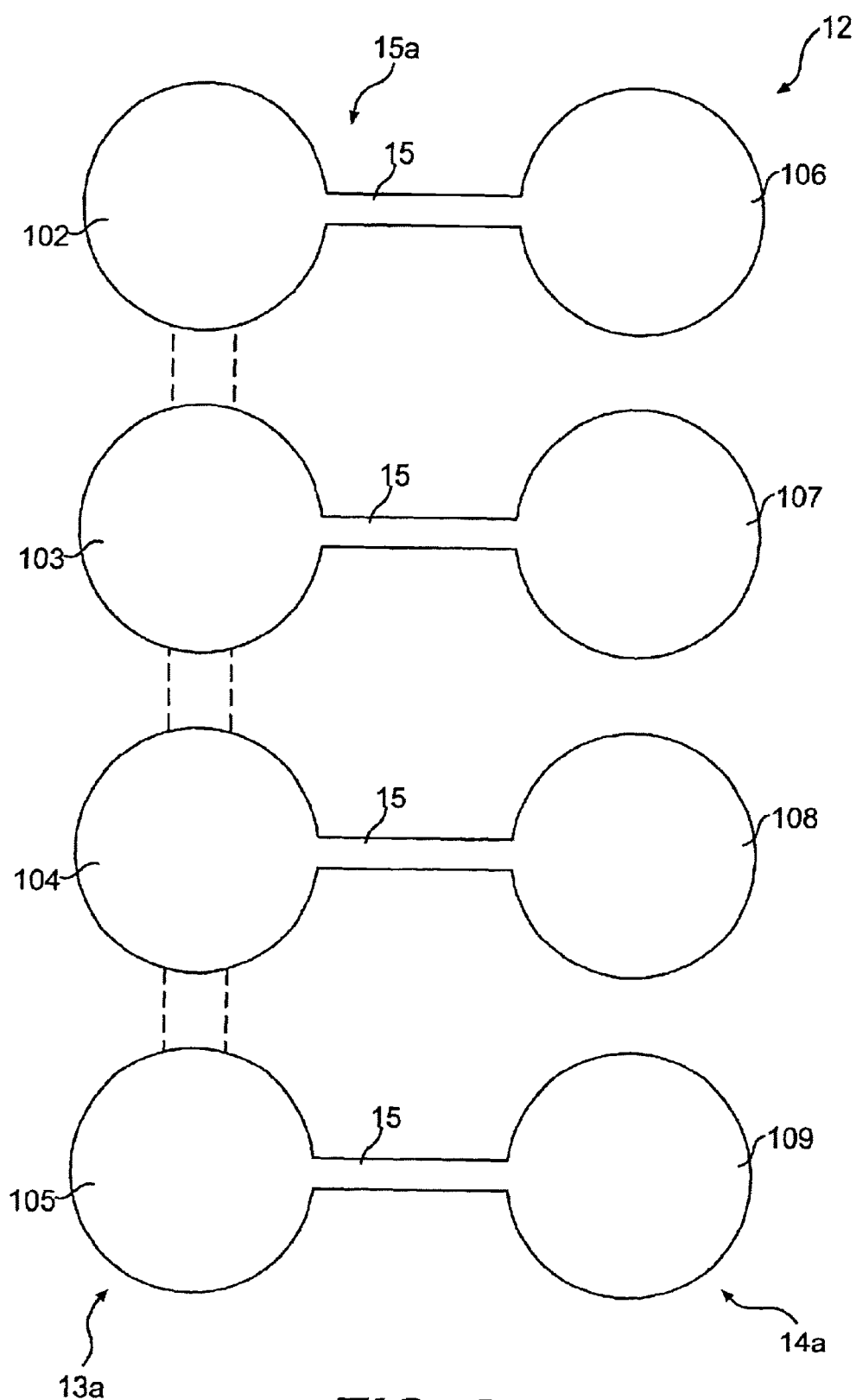
FIG. 9 is a view similar to FIG. 2A, showing an alternative embodiment of a chamber defined in a test device of the present invention, where the first well region and the second well region each define a plurality of wells, and where the channel region defines a plurality of channels joining respective wells of each well region.
Figure 10:
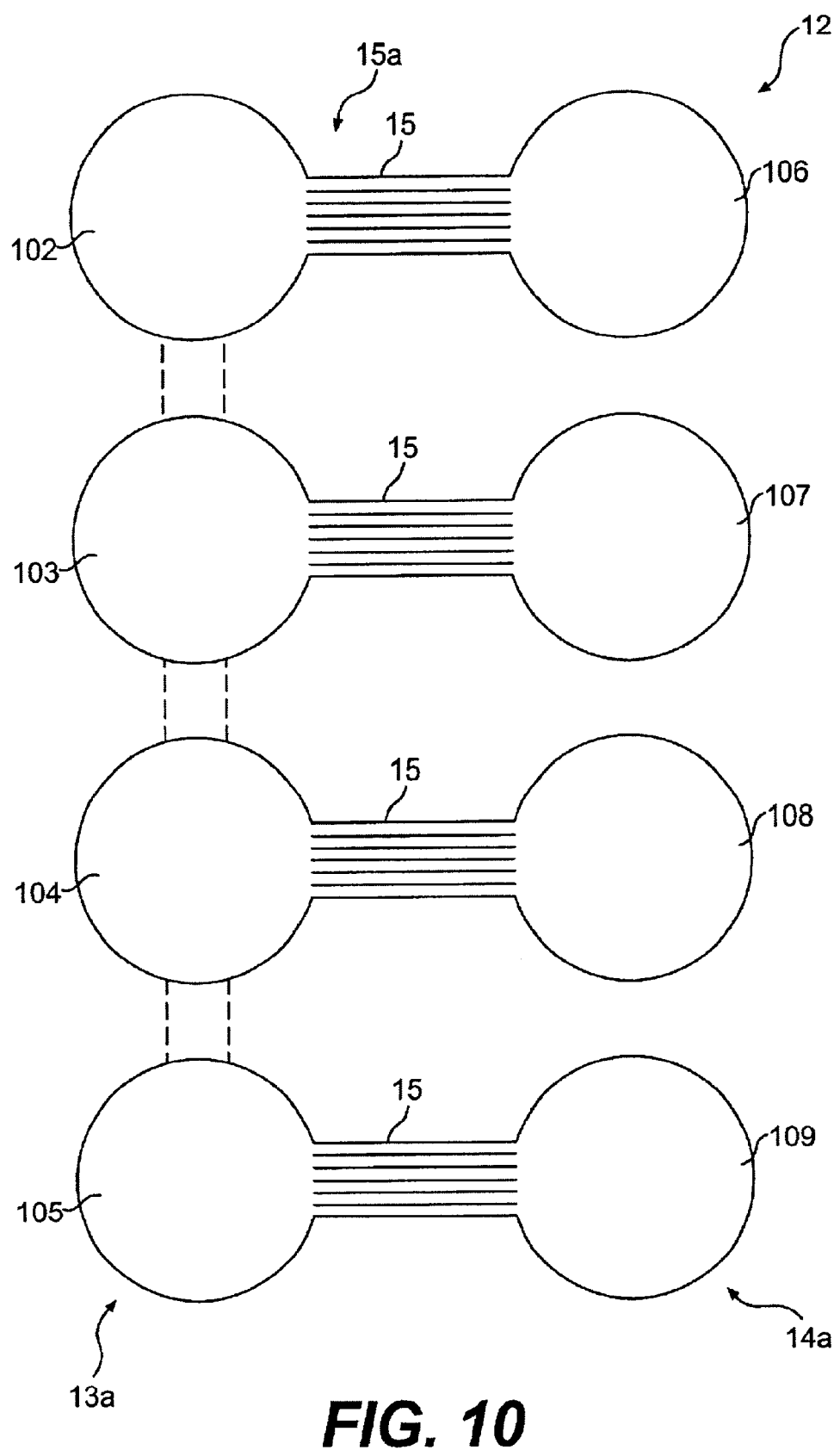
FIG. 10 is a view similar to FIG. 2A, showing an alternative embodiment of a chamber defined in a test device of the present invention, where the channel region defines a plurality of channels joining respective wells of each well region.

In addition to variations of components of a discrete chamber 12, the present invention also contemplates variations in the overall chamber 12 as well as variations from chamber to chamber. With respect to the overall chamber 12, in one embodiment, the chambers 12 are sized so that a complete chamber 12 fits into the area normally required for a single well of a 96-well plate. In this configuration, 96 different assays could be performed in a 96-well plate. In another embodiment, the 1:1 ratio of a first well to second well, as present in the aforementioned embodiments, is altered by modifying chamber 12. For example as seen in FIG. 9, device 10 includes a chamber 12 having a first well region 13a having a plurality of first wells 102, 103, 104 and 105 connected to one another, a second well region 14a having a plurality of wells 106, 107, 108 and 109, and a channel region 15a having a plurality of channels 15 connecting respective ones of the first wells to respective ones of the second wells. Each well of the first well region 13a may receive the same test agent, and each well of the second well region 14a may receive a different cell type. Alternatively, each well of the first well region 13a may receive a different test agent, and each well of the second well region 14a may receive the same cell type. This configuration allows several different cell types or different test agents to be tested simultaneously. In an alternative embodiment as seen in FIG. 10, each channel 15 of channel region 15a comprises subchannels as shown. This arrangement not only allows several different cell types or test agents to be tested simultaneously but also generates several tests of each test agent or cell type.

Figure 11:
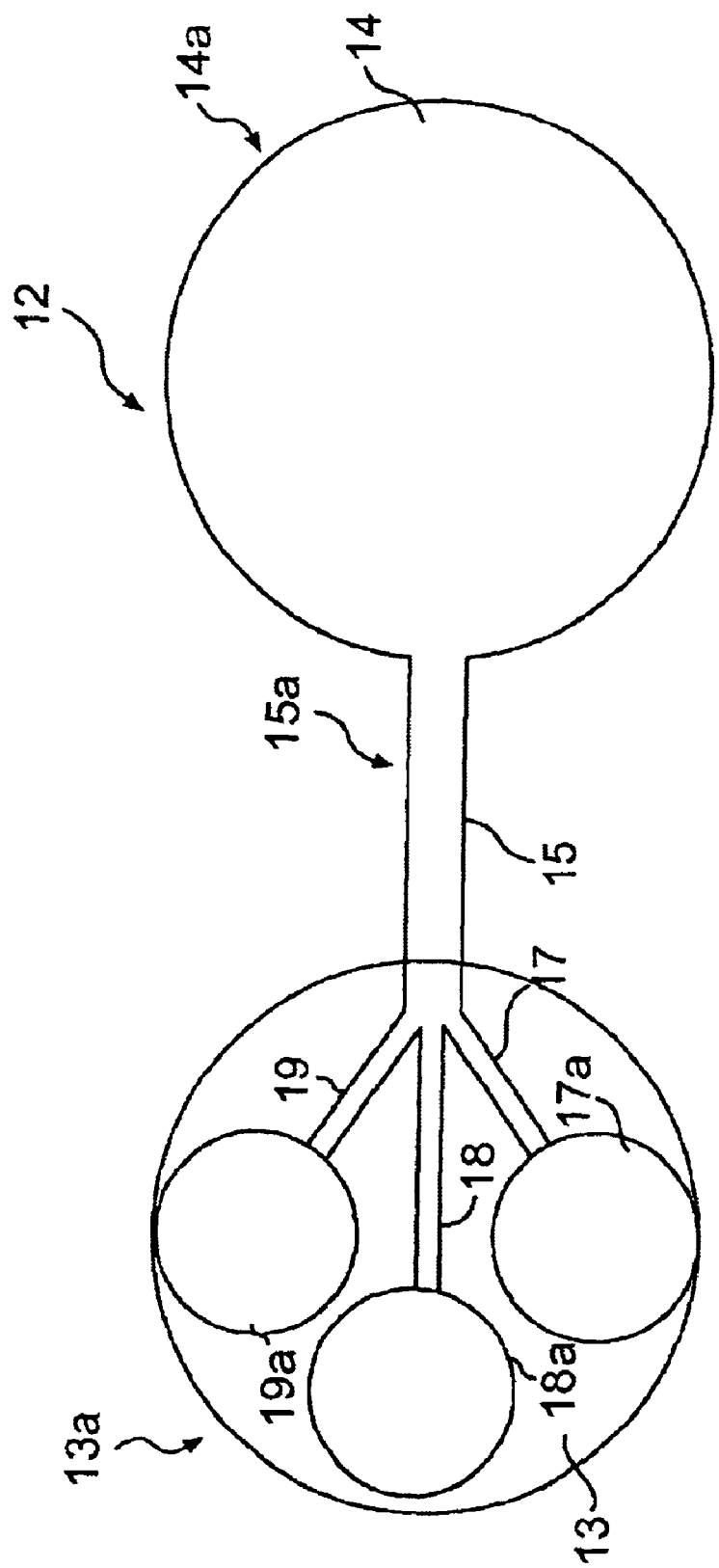
FIG. 11 is a view similar to FIG. 2A, showing an alternative embodiment of a chamber defined in a test device of the present invention, where the first well region has a plurality of wells and a respective capillary for each well, the channel region has a single channel, and the second well region has a single well.

FIG. 11 illustrates an alternative chamber configuration of a test device according to an alternative embodiment of the present invention. In this embodiment, chamber 12 comprises a first well region 13a connected by a channel region 15a including a single channel 15 to a second well region 14a including a single well 14. The first well region contains a plurality of first wells, 17a, 18a, and 19a and a plurality of capillaries, a first perimeter capillary 17, a center capillary 18, and a second perimeter capillary 19 connected to respective ones of the plurality of first wells. All three of the capillaries converge at a junction into channel 15, which is connected with the second well region 14a. Well region 13a is not limited to containing only three capillaries and can contain any number of additional capillaries (not shown). First wells 17a–19a may, for example, be adapted to receive solutions of biomolecules, which are allowed to flow into channel 15 and adsorb nonspecifically to the regions of the surface over which the solution containing the biomolecules flows. First wells 17a–19a are also adapted to subsequently receive cells. With respect to variations from chamber to chamber, in one embodiment, the length L of each channel 15 increases along one or more dimensions of top member 11 from one chamber to the adjacent chamber. In an alternative embodiment, all chambers 12 have channel 15 of the same length L. The width W of each channel 15 can also vary and can increase along one or more dimensions of top member 11 from one chamber to the adjacent chamber. In an alternative embodiment, all chambers 12 have channel 15 of the same width W. FIG. 4A is a top plan view of an embodiment of the present invention where, within top member 11, different chambers have various channel sizes and shapes, such sizes and shapes being in no particular order, pattern, or arrangement. By employing this varied configuration, the best channel region design for a given test may be obtained. In other words, where the optimal channel region design is determined, a new assay plate configured solely to those specifications may be employed.

Support member 16 of device 10 provides a support upon which top member 11 rests and can be made of any material suitable for this function. Suitable materials are known in the art such as glass, polystyrene, polycarbonate, PMMA, polyacrylates, and other plastics. Where device 10 is a chemotaxis, haptotaxis and/or chemoinvasion device, it is preferable that support member 16 comprise a material that is compatible with cells that may be placed on the surface of support member 16. Suitable materials may include standard materials used in cell biology, such as glass, ceramics, metals, polystyrene, polycarbonate, polypropylene, as well as other plastics including polymeric thin films. A preferred material is glass with a thickness of about 0.1 to about 2 mm, as this may allow the viewing of the cells with optical microscopy techniques.

Similar to top member 11, support member 16 can have several different embodiments. In particular, the configuration and surface treatment of support member 16 may vary.

Figure 12:
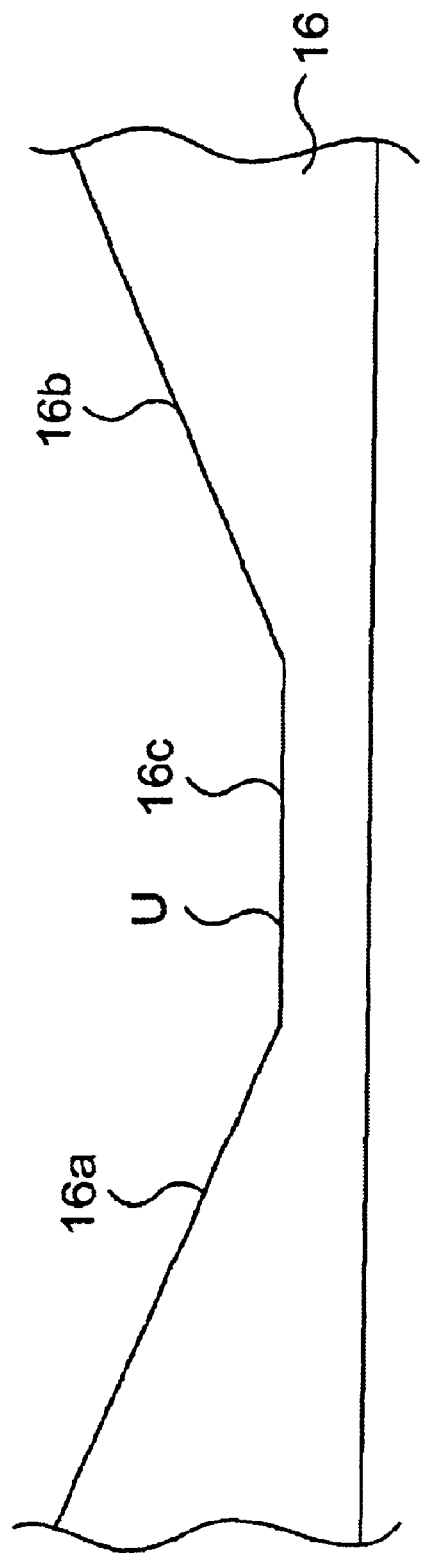
FIG. 12 is a side, cross-sectional view of an embodiment of a portion of the support member according to the present invention, the portion of the support member being shown along a longitudinal axis of a chamber according to the present invention.

As seen in a side view of support member 16 in FIG. 12, the upper surface U of support member 16, which underlies top member 11, may be sloped at predetermined regions thereof with respect to a horizontal plane at less than a 90° angle. In the shown embodiment, the predetermined regions correspond to bottom surfaces of respective wells, surface 16a corresponding to a bottom surface of a well 13, and surface 16b corresponding to a bottom surface of well 14. Surface 16c, in turn, corresponds to a bottom surface of channel 15. In this embodiment, the given configuration facilitates suspended cells flowing in the direction of the downward slope of top surface 16b of support member 16 to become more readily exposed to the concentration gradient. If a soluble test substance is used as the test agent in well 13 of device 10, then top surface 16a of support member 16 may also be downwardly sloped with respect to a horizontal plane at less than a 90° angle to facilitate exposure of the test substance to channel 15 in order to facilitate formation of the solution concentration gradient.

Support member 16 may also have a treatment on or embedded into its surface. This treatment may serve numerous functions, including, for example, facilitating the placement, adhesion or movement of cells being studied, and simulating in vivo conditions. Numerous surface configurations and chemicals may be used alone or in conjunction for this treatment. For example, in one embodiment support member 16 includes a patterned self-assembled monolayer (SAM) on a gold surface or other suitable material. SAMs are monolayers typically formed of molecules each having a functional group that selectively attaches to a particular surface, the remainder of each molecule interacting with neighboring molecules in the monolayer to form a relatively ordered array. By using SAMs, various controls of biological interactions may be employed. For example, SAMs may be arrayed or modified with various "head groups" to produce "islands" of biospecific surfaces surrounded by areas of bio-inert head groups. Further, SAMs may be modified to have "switchable surfaces" that may be designed to capture a cell and then be subsequently modified to release the captured cell. Moreover, it may also be desirable to utilize a bioinert support member material to resist non-specific adsorption of cells, proteins, or any other biological material. Consequently, the use of SAMs on support member 16 may be advantageous.

Figure 13:
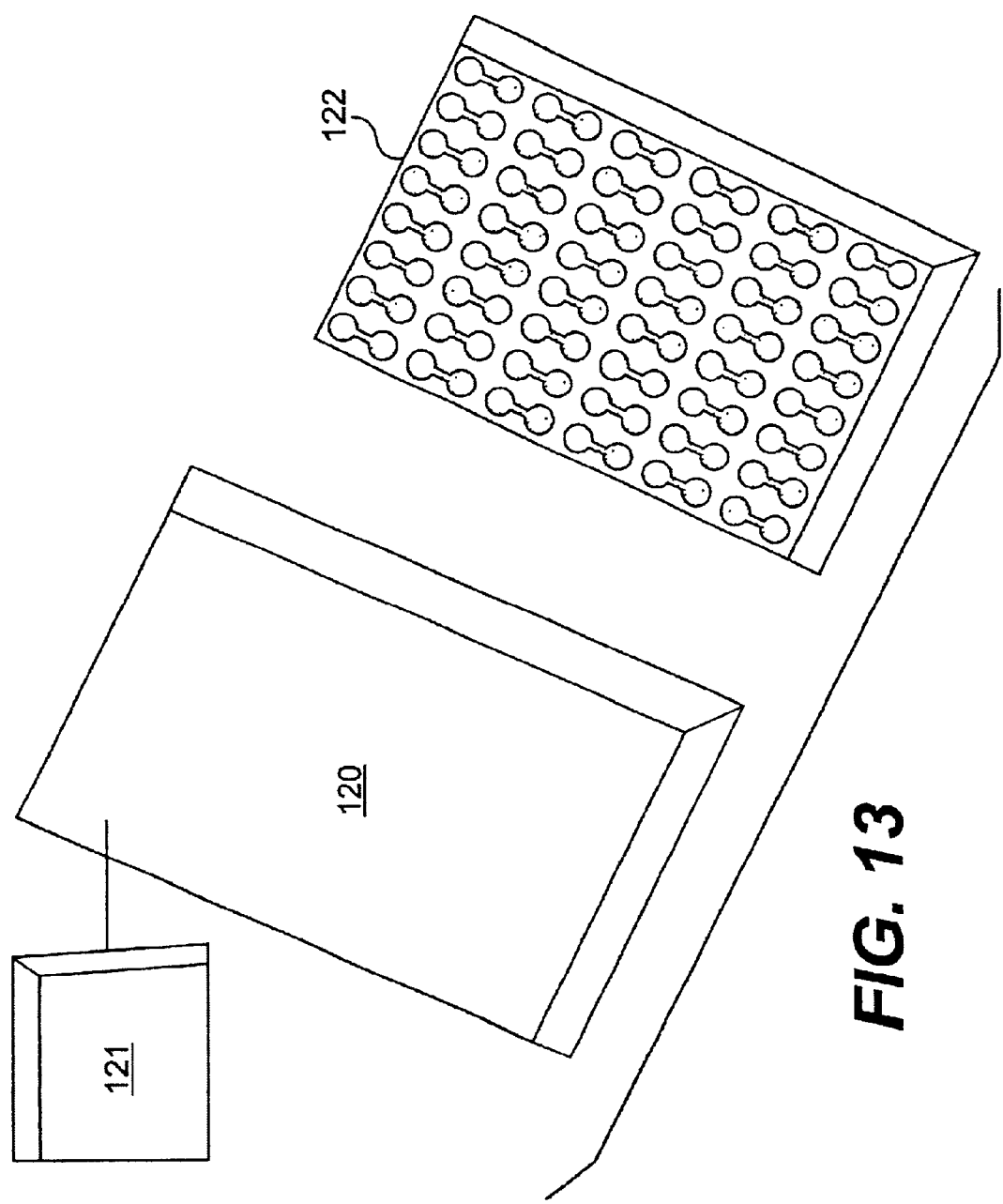
FIG. 13 is an isometric view of a collective system according to one embodiment of the present invention.

The present invention also contemplates, as seen in FIG. 13, the use of any system known in the art to detect and analyze cell chemotaxis, haptotaxis, and chemoinvasion. In particular, the present invention contemplates the use of any system known in the art to visualize changes in cell morphology as cells move across channel 15, to measure the distance cells travel in channel 15, and to quantify the number of cells that travel to particular points in channel 15. As such the present invention contemplates both "real-time" and "endpoint" analysis of chemotaxis, haptotaxis, and chemoinvasion. In one embodiment, the device 122 includes an observation system 120 and a controller 121. The controller 121 is in communication with the observation system 120 via line 122. The controller 121 and observation system 120 may be positioned and programmed to observe, record, and analyze chemotaxis and chemoinvasion of the cells in the device. The observation system 120 may be any of numerous systems, including a microscope, a high-speed video camera, and an array of individual sensors. Nonlimiting examples of microscopes include phase-contrast, fluorescence, luminescence, differential-interference-contrast, dark field, confocal laser-scanning, digital deconvolution, and video microscopes. Each of these embodiments may view or sense the movement and behavior of the cells before, during, and after the test agent is introduced. At the same time, the observation system 120 may generate signals for the controller 121 to interpret and analyze. This analysis can include determining the physical movement of the cells over time as well as their change in shape, activity level or any other observable characteristic. In each instance, the conduct of the cells being studied may be observed in real time, at a later time, or both. The observation system 120 and controller 121 may provide for real-time observation via a monitor. They may also provide for subsequent playback via a recording system of some kind either integrated with these components or coupled to them. For example, in one embodiment, cell behavior during the desired period of observation is recorded on VHS format videotape through a standard video camera positioned in the vertical ocular tubes of a triocular compound microscope or in the body of an inverted microscope and attached to a high quality video recorder. The video recorder is then played into a digitization means, e.g., PCI frame grabber, for the conversion of analog data to digital form. The electronic readable (digitized) data is then accessed and processed by an appropriate dynamic image analysis system, such as that disclosed in U.S. Pat. No. 5,655,028 expressly incorporated in its entirety herein by reference. Such a system is commercially available under the trademark DIAS® from Solltech Inc. (Oakland, Iowa). Software capable of assisting in discriminating cells from debris and other detection artifacts that might be present in the sample should be particularly advantageous. In either case, these components may also analyze the cells as they progress through their reaction to the test agent.

Figure 15:
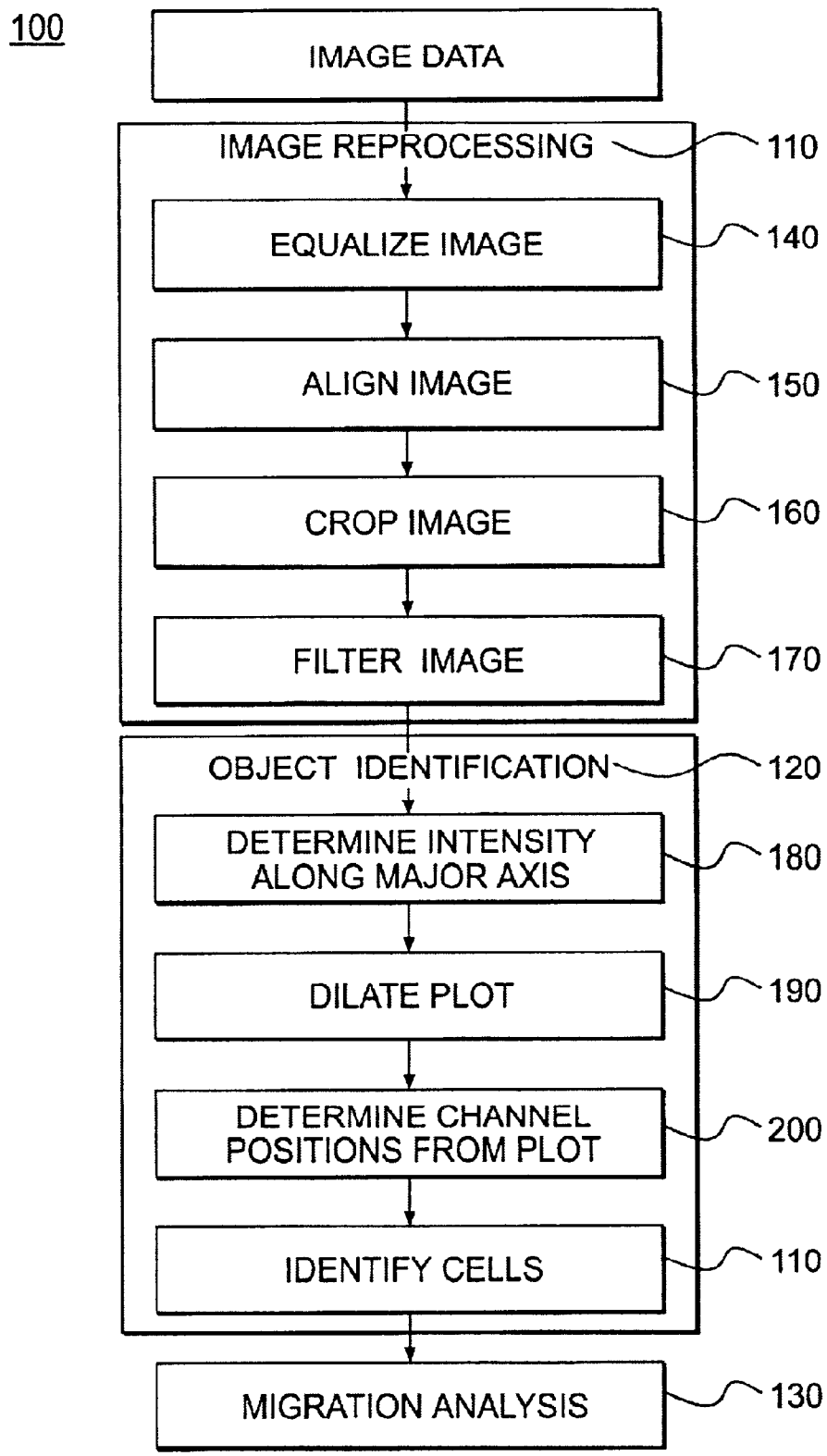
FIG. 15 is a block diagram of an automated analysis system according to an embodiment of the present invention.

In one embodiment, the present invention contemplates the use of an automated analysis system, as illustrated in FIG. 15, to analyze data measuring the distance cells travel in channel 15, and to quantify the number of cells that travel to particular points in channel 15. FIG. 15 is a block diagram of an automated analysis system 100 including, for example, an image preprocessing stage 110, an object identification stage 120 and a migration analysis stage 130. The image preprocessing stage 110 may receive digital image data of chamber 12 from a digital camera or other imaging apparatus as described above. The data typically includes a plurality of image samples at various spatial locations (called, "pixels" for short) and may be provided as color or grayscale data. The image preprocessing stage 110 may alter the captured image data to permit algorithms of the other stages to operate on it. The object identification stage 120 may identify objects from within the image data. Various objects may be identified based on the test to be performed. For example, the object identifier may identify channels 15, cells or cell groups from within the image data. The migration analysis stage 130 may perform the migration analysis designated for testing. FIG. 15 illustrates a number of blocks that may be included within the image preprocessing stage 110. Essentially, the image preprocessing stage 110 counteracts image artifacts that may be present in the captured image data as a result of imperfections in the imager or the device. In one embodiment, the image preprocessing stage 110 may include an image equalization block 140. The equalization 140 may find application in embodiments where sample values of captured image data do not occupy the full quantization range available for the data. For example, an 8-bit grayscale system permits 256 different quantization levels for input data (0–255). Due to imperfections in the imaging process, it is possible that pixel values may be limited to a narrow range, say the first 20 quantization levels (0–20). The equalization 140 may re-scale sample values to ensure that they occupy the full range available in the 8-bit system.

In another embodiment, the equalization block 140 may re-scale sample values based on a color or wavelength. Conventional cellular analysis techniques often cause cells to appear in predetermined colors or with predetermined wavelengths, which permits them to be distinguished from other materials captured by the imager. For example, in fluorescent applications, cells emit light at predetermined wavelengths. In nuclear staining applications, cell nuclei are dyed with a material that causes them to appear in the image data with predetermined colors. The equalization block 140 may re-scale sample values having components that coincide with these expected colors or wavelengths. In so doing, the equalization block 140 effectively filters out other colors or wavelengths, a consequence that may be advantageous in later image processing.

Figure 16:
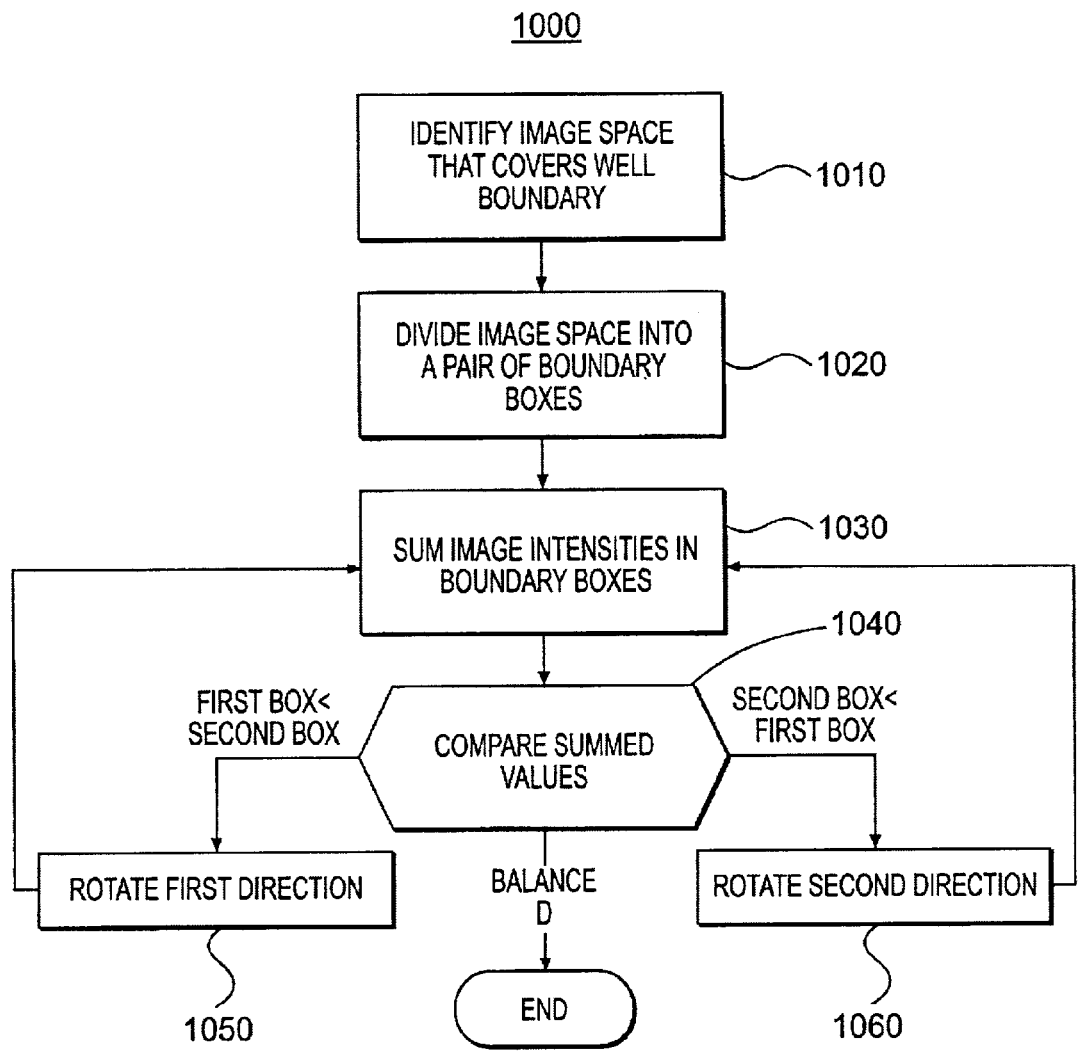
FIG. 16 is a flow diagram of a method according to an embodiment of the present invention.
Figure 17:
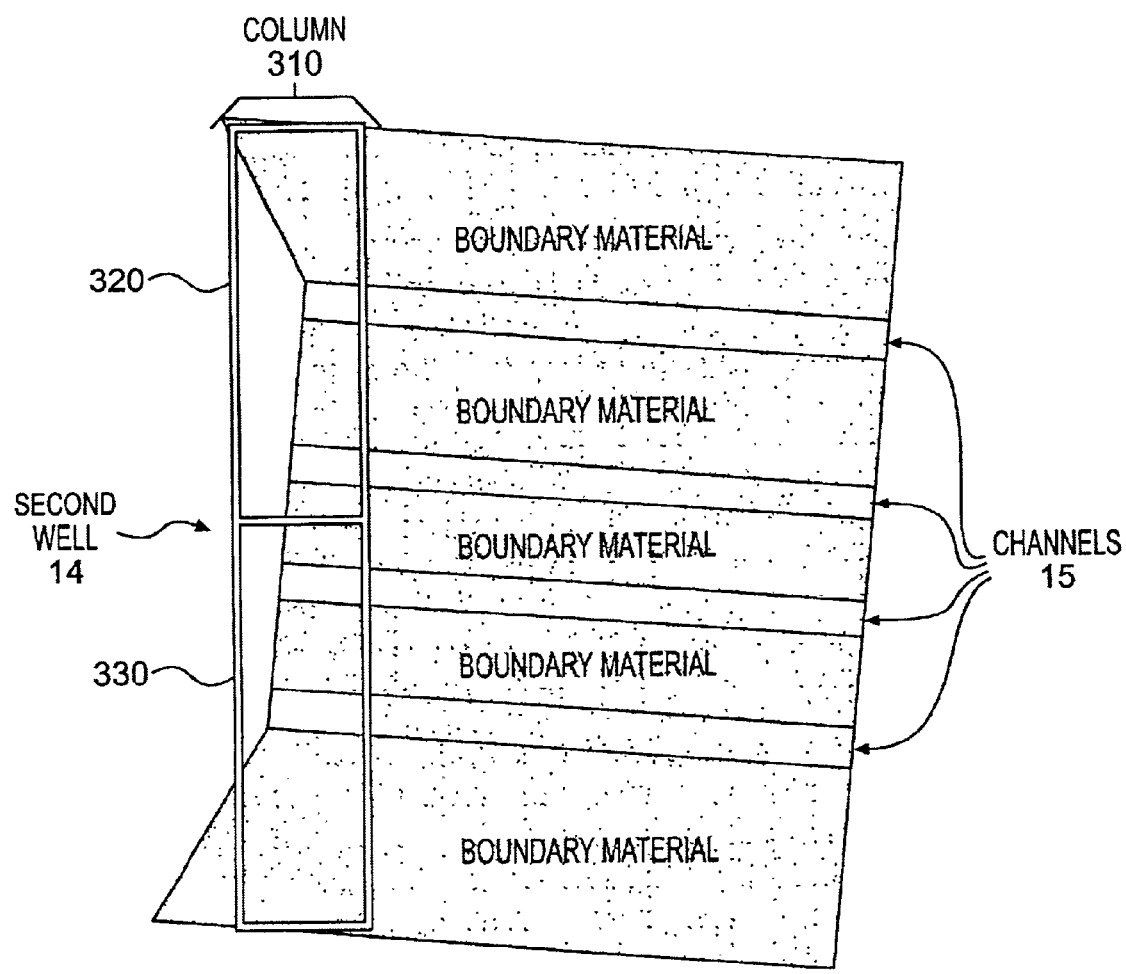
FIG. 17 illustrates exemplary image data on which the method of FIG. 16 may operate.
Figure 18:
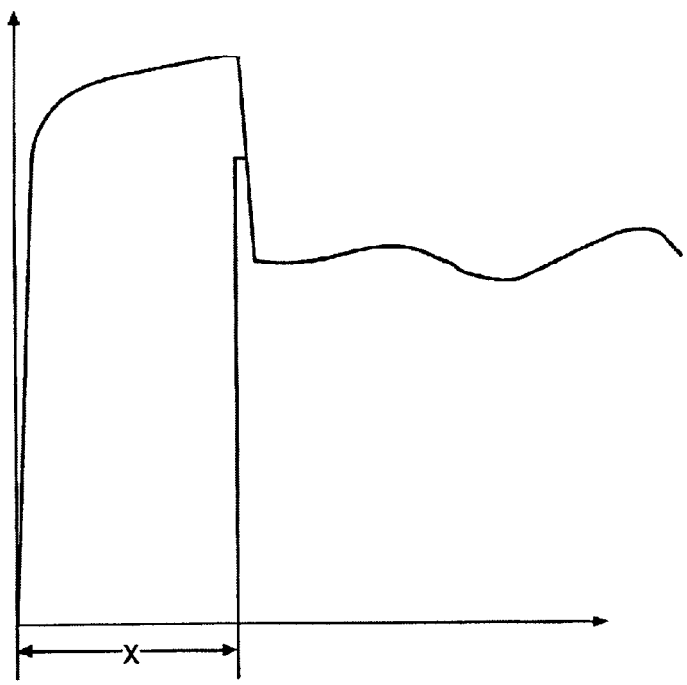
FIG. 18 illustrates a histogram that may be obtained from the image data of FIG. 17.

Image rotation is another image artifact that may occur from imperfect imaging apparatus. Although the channels 15 are likely to be generally aligned with columns and rows of pixels in the image data, further analysis may be facilitated if the alignment is improved. Accordingly, in an embodiment, the image preprocessing stage 110 may include an image alignment block 150 that rotates the captured image data to counteract this artifact. Once the rotation artifact has been removed from the captured image data, then image from individual channels 15 are likely to coincide with a regular row or column array of pixel data. FIG. 16 illustrates a method of operation for the image alignment block 150 according to an embodiment of the present invention and described in connection with exemplary image data illustrated in FIG. 17. In the example of FIG. 17, channels 15 are aligned generally with rows of image data but for the rotation artifact. To counteract the rotation artifact, the image preprocessor may identify a band of image data coinciding with a boundary between second well 14 and the channels 15 themselves (block 1010). In the case of FIG. 17, the band may constitute column 310. Generally, the area of second well 14 will be bright relative to the area of channels 15 due the greater number of cells present therein. Thus, a histogram of image data values along a presumed direction of the channels 15 may appear as shown in FIG. 18. The band 310 may be identified from an abrupt change in image data values along this direction.

Having identified a column of image data to be considered, the column 310 may be split into two boundary boxes 320, 330 (block 1020). By summing the intensity of the image data in each of the two boundary boxes and comparing summed values to each other, an orientation of the rotation artifact may be determined (blocks 1030, 1040). In the example of FIG. 17, the rotation artifact causes more of second well 14 to fall within the area of boundary box 320 than of boundary box 330 (a clockwise artifact). The image data may be rotated counterclockwise until the summed values of each boundary box 320, 330 become balanced.

Thus, if the image intensity of the first bounding box is greater than that of the second bounding box 330, the image data may be rotated in a first direction (block 1050). If the image intensity of the second bounding box 330 is greater than that if the first bounding box 320, the image data may be rotated in a second direction (block 1060). And when the image intensities are balanced, the method 1000 may conclude; the rotation artifact has been corrected.

Returning to FIG. 15, the image preprocessing stage 110 also may process the captured image data by cropping the image to the area occupied by channels 15 themselves (block 160). As described, each test bed may include a pair of wells interconnected by a plurality of channels. For much of the migration analysis, it is sufficient to measure cellular movement or activity within channels 15 only. Activity in second well 14 or the first well 13 need not be considered. In such an embodiment, the image preprocessing stage 110 may crop the image data to remove pixels that lie outside channels 15.

Figure 19:
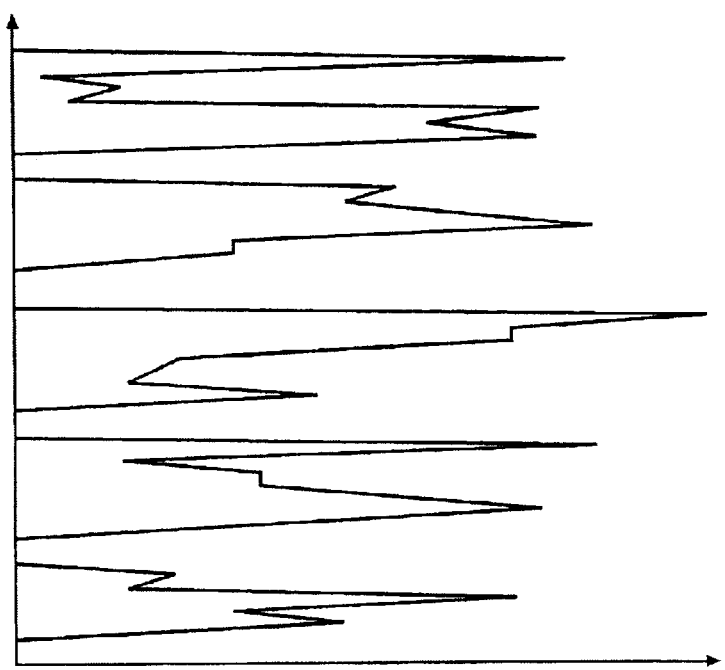
FIG. 19 illustrates exemplary image data.
Figure 20:
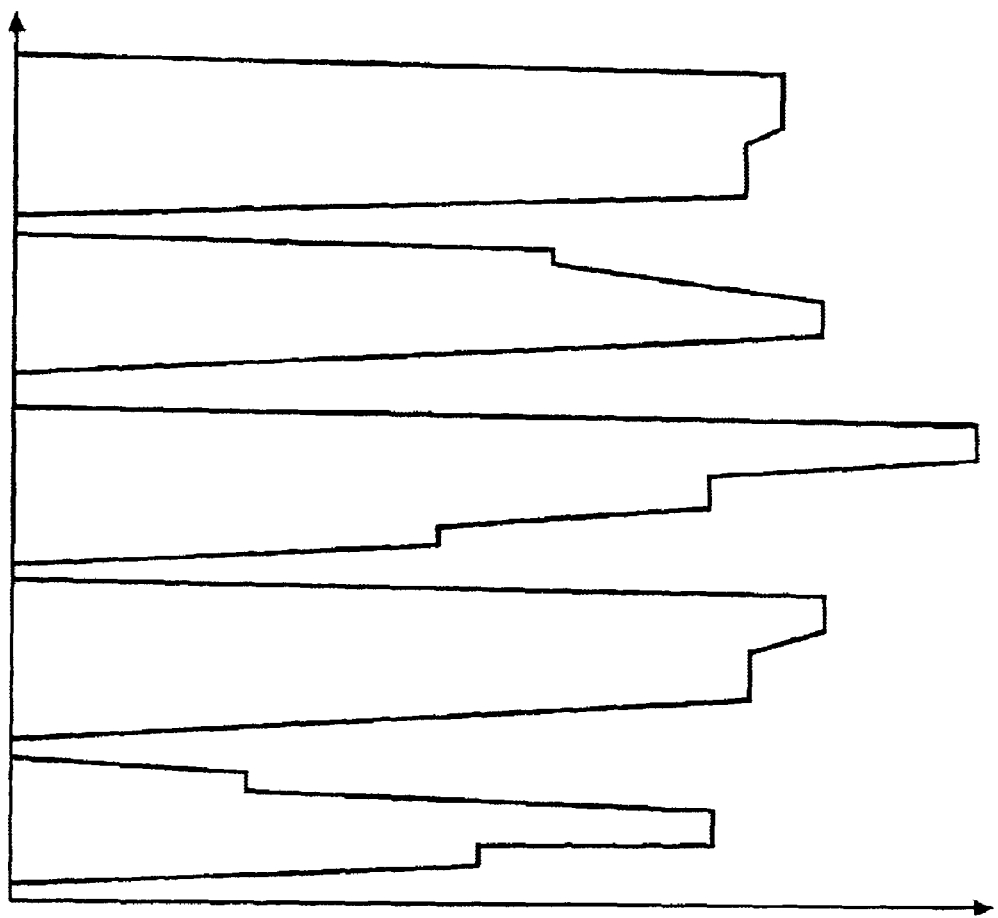
FIG. 20 illustrates exemplary dilated image data.

The image preprocessing stage 110 also may include a thresholding block 170, performing threshold detection upon the image data. The thresholding block 170 may truncate to zero any sample having a re-scaled value that fails to exceed a predetermined threshold. Such thresholding is useful to remove noise from the captured image data. In an embodiment, the thresholding block 170 may be integrated with the equalization block 140 discussed above. It need not be present as a separate element. In some embodiments, particularly those where the equalization block 140 scales pixel values according to wavelength components, the thresholding block 170 may be omitted altogether. An output of the image preprocessing stage 110 may be input to the object identification stage 120. The object identification stage 120 identifies objects from within the image data, including the microchannels themselves and, optionally, individual cells. According to an embodiment, in a fluorescent system, channels 15 may be identified by developing a histogram of the fluorescent light along a major axis in the system (block 180). FIG. 19 illustrates image data that may have been determined from the example of FIG. 17. The major axis may coincide with the boundary between the second well adapted to receive a sample comprising cells and the channel region. Light intensity from within channel region 15a area may be summed along this axis, yielding a data set represented in FIG. 19. In a second stage, the data set is "dilated" (block 190). Dilation may be achieved by applying a high pass filter to the data set or any other analogous technique. FIG. 20 illustrates the data set of FIG. 19 having been subject to dilation.

From the data set of FIG. 20, the channels may be identified. Candidate channel 15 positions may be identified to coincide with relative maximums of the data set. Alternatively, candidate positions of boundaries between channels 15 may be determined from relative minimums from within the data set of FIG. 20. A final set of channel 15 positions may be determined from a set of parameters known about channel region 15a itself. For example, if channels 15 are known to have been provided with a regular spacing among channels 15, any candidate channel 15 position that would violate the spacing can be eliminated from consideration.

Returning to FIG. 15, in addition to identifying channels 15, individual cells may be identified within the image data (block 200). In an application where cells are marked with nuclear staining, identification of individual cells merely requires an image processor to identify and count the number of marked nuclei. The nuclei appear is a number of dots of a predetermined color. In an application using fluorescing cells, identification of individual cells becomes more complicated. Individual cells can be identified relatively easily; they appear as objects of relatively uniform area in the image data. Identifying a number of cells clustered together becomes more difficult. In this case, the number of cells may be determined from the area or radius of the cluster in the image data. The cluster is likely to appear in the image having some area or cluster radius. By comparing the cluster's area or radius to the area or radius of an individual cell, the number of cells may be interpolated. Of course, identification of individual cells may be omitted depending upon the requirements of the migration analysis.

The final stage in the image processing system is the migration analysis 130 itself. In one embodiment, coordinate data of each cell in the channels 15 may be gathered and recorded. However, some testing need not be so complicated. In a first embodiment, it may be sufficient merely to identify the number of cells present in channel 15. In this case, identification of individual cells may be avoided by merely summing quantities of fluorescent light detected in each channel 15. From this measurement, the number of cells may be derived without investing the processing expense of identifying individual cells. The foregoing description presents image analysis that is relevant to a single channel 15 to be tested. Of course, depending upon the requirements of the migration analysis 130, it may be desired to generate image samples of a number of different channels 15. Further, it may be desirable to generate image samples of a single channel 15 at different times. The image processing described above may be repeated for different channels 15 and different times to accommodate for such test scenarios.

According to an embodiment, the image processing may account for manufacturing defects of individual channels 15. During image processing, manufacturing defects may prevent cell migrations into a channel 15. In an embodiment, when the system 100 counts a number of cells in the channel 15 (or derives the number from identified cell locations), it may compare the number to an expectation threshold. If the number is below the expectation threshold, the system 100 may exclude the channel 15 from migration analysis. In practice, this expectation threshold may be established as a minimum number of cells that are likely to enter a properly configured cell given the test conditions being analyzed under the migration analysis. If the actual number of cells falls below this threshold, it may lead to a conclusion that channel 15 blocking conditions may be present.

The foregoing operations and processes of the analysis system 100 may be performed by general purpose processing apparatus, such as computers, workstations or servers, executing software. Alternatively, some of the operations or processes may be provided in a digital signal processor or application specific integrated circuit (colloquially, an "ASIC"). Additionally, these operations and processes, particularly those associated with image preprocessing, may be distributed in processors of a digital microscope system. Such variations are fully within the scope of the present invention.

The present invention also contemplates the use of the aforementioned embodiments of device 10 to assay various elements of chemotaxis, haptotaxis and chemoinvasion. In general, the present invention provides for a first assay comprising high throughput screening of test agents to determine whether they influence chemotaxis, haptotaxis, and chemoinvasion. Test agents generally comprise either soluble test substances or immobilized test biomolecules and are generally placed in first well region 13a of chamber 12 of device 10. After determining which test agents influence chemotaxis, by acting as chemoattractants and promoting or initiating chemotaxis, by acting as chemorepellants and repelling chemotaxis, or by acting as inhibitors and halting or inhibiting chemotaxis, then a second assay can be performed screening test compounds. The test compounds generally comprise therapeutics or chemotaxis/haptotaxis inhibitors and are generally introduced in second well region 14a, which contains a biological sample of cells. The test compounds are screened to determine if and how they influence the cells' chemotaxis or haptotaxis in response to the test agents.

In particular, a chemotaxis/haptotaxis and/or chemoinvasion assay according to an embodiment of the present invention involves a device 10 including a housing comprising a top member 11 mounted to a support member 16. The top member and the support member are configured such that they together define a discrete assay chamber 12. The discrete assay chamber 12 includes a first well region 13a connected by a channel 15 to a second well region 14a. The first well region 13a includes at least one first well 13, each of the at least one first well 13 being adapted to receive a test agent therein. The second well region 14a includes at least one second well 14 horizontally offset with respect to the first well region 13a in a test orientation of the device, each of the at least one second well 14 being adapted to receive a cell sample therein. Channel 15 includes at least one channel connecting the first well region 13a and the second well region 14a to one another. The test agent received in first well 13 is a soluble test substance and/or immobilized test biomolecules. When the test agent comprises immobilized test biomolecules, the biomolecules are immobilized on an upper surface U of support member 16 constituting the bottom surface of well region 13a as well as on upper surface U of support member 16 constituting the bottom surface of channel region 15a.

Nonlimiting examples of biological samples of cells include lymphocytes, monocytes, leukocytes, macrophages, mast cells, T-cells, B-cells, neutrophils, basophils, eosinophils, fibroblasts, endothelial cells, epithelial cells, neurons, tumor cells, motile gametes, motile forms of bacteria, and fungi, cells involved in metastasis, and any other types of cells involved in response to inflammation, injury, or infection. Well region 14a may receive only one cell type or any combination of the above-referenced exemplary cell types. For example, as described above, it is often desirable to provide a mixed cell population to more effectively create an environment similar to in vivo conditions. Well region 14a may also receive cells at a particular cell cycle phase. For example, well region 14a may receive lymphocytes in $G_1$ phase or $G_0$ phase.

Nonlimiting examples of soluble test substances include chemoattractants, chemorepellants, or chemotactic inhibitors. As explained above, chemoattractants are chemotactic substances that attract cells and once placed in well region 14a, cause cells to migrate towards well region 14a. Chemorepellents are chemotactic substances that repel cells and once placed in well region 14a, cause cells to migrate away from well region 14a. Chemotactic inhibitors are chemotactic substances that inhibit or stop chemotaxis and once placed in well region 14a, cause cells to have inhibited migration or no migration from well region 14a. Nonlimiting examples of chemoattractants include hormones such as $T_3$ and $T_4$, epinephrine and vasopressin; immunological agents such as interleukein-2, epidermal growth factor and monoclonal antibodies; growth factors; peptides; small molecules; and cells. Cells may act as chemoattractants by releasing chemotactic factors. For example, in one embodiment, a sample including cancer cells may be added to well 13. A sample including a different cell type may be added to well 14. As the cancer cells grow they may release factors that act as chemoattractants attracting the cells in well 14 to migrate towards well 13. In another embodiment, endothelial cells are added to well 13 and activated by adding a chemoattractant such as TNF-α or IL-1 to well 13. Leukocytes are added to well 14 and may be attracted to the endothelial cells in well 14.

Non-limiting examples of chemorepellants include irritants such as benzalkonium chloride, propylene glycol, methanol, acetone, sodium dodecyl sulfate, hydrogen peroxide, 1-butanol, ethanol, and dimethylsulfoxide; and toxins such as cyanide, carbonylcyanide chlorophenylhydrazone, endotoxins and bacterial lipopolysaccharides; viruses; pathogens; and pyrogens.

Nonlimiting examples of immobilized biomolecules include chemoattractants, chemorepellants, and chemotactic inhibitors as described above. Further non-limiting examples of immobilized chemoattactants include chemokines, cytokines, and small molecules. Further non-limiting examples of chemoattractants include IL-8, GCP-2, GRO-α, GRO-β, MGSA-β, MGSA-γ, $PF_4$, ENA-78, GCP-2, NAP-2, IL-8, IP10, I-309, I-TAC, SDF-1, BLC, BRAK, bolekine, ELC, LKTN-1, SCM-1β, MIG, MCAF, LD7α, eotaxin, IP-110, HCC-1, HCC-2, Lkn-1, HCC-4, LARC, LEC, DC-CK1, PARC, AMAC-1, MIP-2β, ELC, exodus-3, ARC, exodus-1, 6Ckine, exodus 2, STCP-1, MPIF-1, MPIF-2, Eotaxin-2, TECK, Eotaxin-3, ILC, ITAC, BCA-1, MIP-1α, MIP-1β, MIP-3α, MIP-3β, MCP-1, MCP-2, MCP-3, MCP-4, MCP-5, RANTES, eotaxin-1, eotaxin-2, TARC, MDC, TECK, CTACK, SLC, lymphotactin, and fractalkine; and other cells. Further non-limiting examples of chemorepellants include receptor agonists and other cells.

In order to perform a test, such as a chemotaxis and/or chemoinvasion assay utilizing a soluble test substance, the test device 10 is first fabricated. A preferred embodiment of the method of making the device according to the present invention will now be described. A master that is the negative of top-plate 11 is fabricated by standard photolithographic procedures. A predetermined material is spin coated or injection molded onto the master. The predetermined material is then cured, peeled off the master to comprise top member 11 and placed onto support member 16.

Where the test device 10 is a chemotaxis, haptotaxis and/or chemoinvasion device, a rigid frame with the standard microtiter footprint is preferably placed around the outer perimeter of top member 11. In one embodiment, a gel matrix is poured into well region 13a and allowed to flow into channel region 15a. After the gel matrix sets, excess gel is removed from well regions 13a and 14a. In another embodiment, no gel matrix is added to channel region 15a. Subsequently, a biological sample of cells is placed in well region 14a and a test substance is placed in well region 13a. In one embodiment, a low concentration of a test substance is placed in well region 14a in order to activate the cells and expedite the beginning of the assay. Alternatively, depending on the cells being studied and the soluble test substance being used, the soluble test substance may be introduced during or after the cells have been placed in well region 14a. Once the soluble test substance has been introduced, by the process of diffusion, a solution concentration gradient of the test substance forms along the longitudinal axis of channel region 15a from well region 13a containing the test agent towards well region 14a containing the biological sample of cells. A secondary effect of this solution gradient is the formation of a physisorbed (immobilized) gradient. When this solution gradient is established, some fraction of the solute of the test substance may adsorb onto support member 16. This adsorbed layer of test solute may also contribute to chemotaxis and chemoinvasion. The biological sample of cells may respond to this concentration gradient and migrate towards the higher concentration of the test substance, migrate away from the higher concentration of the test substance, or exhibit inhibited movement in response to the higher concentration of the test substance. It is through this chemotaxis in response to the gradient, that the chemotactic influence of the chemotactic substance can be measured. Chemotaxis is assayed by measuring the distance the cells travel and the amount of time the cells take to reach a predetermined point in the channel region 15a or the distance the cells travel and the amount of time the cells take to reach a certain point in well region 14a (in the case of a chemorepellant that causes cells to move away from the chemotactic substance).

Figure 14:
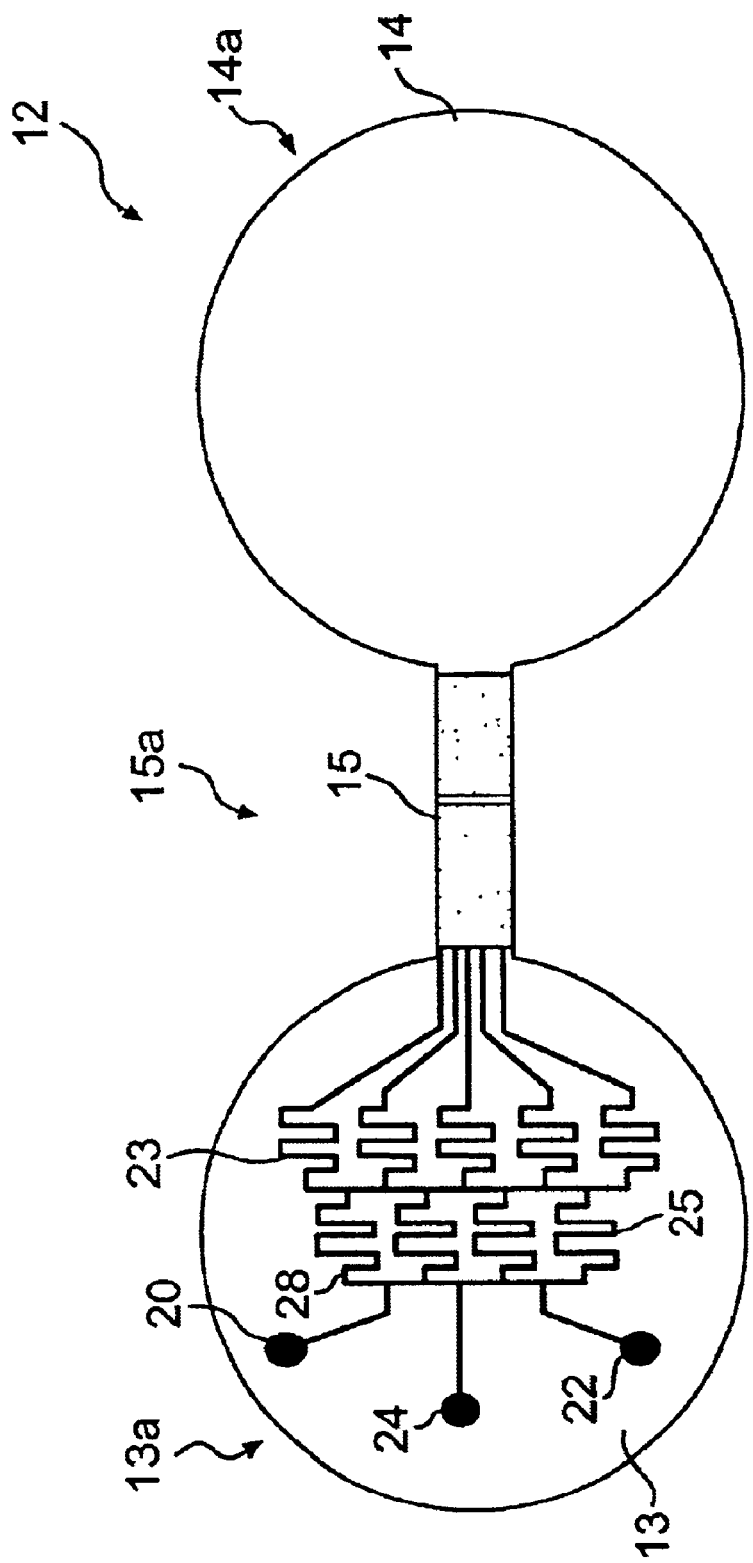
FIG. 14 is a view similar to FIG. 2A, showing an alternative embodiment of a chamber defined in a test device of the present invention, where the first well region includes a plurality of wells interconnected by a network of capillaries, where the channel region includes a single channel, and where the second well includes a single well.

Utilizing an alternative embodiment of device 10 containing an alternative design of chamber 12, a solution concentration gradient is formed using a network of microfluidic channel regions. In this embodiment as seen in FIG. 14, first well region well region 13a of chamber 12 has first wells, 20, 21, and 22, connected by a network of microfluidic capillaries 23 to channel 15. In particular, first well region 13a includes a plurality of first wells connected by a plurality of capillaries 24 connected to respective ones of the plurality of first wells and a plurality of subcapillaries 25 branched off such that each of the plurality of subcapillaries is connected to each of the plurality of capillaries at one end thereof and to channel 15 at another end thereof. Each first well, 20, 21, and 22, receives a different concentration of soluble test substance. After the three first wells, 20, 21, and 22 are simultaneously infused with the three different concentrations of soluble test substance, the solution streams travel down the network of channel regions, continuously splitting, mixing and recombining. After several generations of branched subcapillaries, each subcapillary containing different proportions of soluble test substances are merged into a single channel 15, forming a concentration gradient across channel 15, perpendicular to the flow direction.

According to one embodiment of the present invention, biomolecules are immobilized onto support member 16, preferably on the portion of upper surface U constituting the bottom surface of channel 15 and of well region 13a in any one of the embodiments of the test device of the present invention, such as the embodiments shown in FIGS. 1A–14. The concentration of biomolecules increases or decreases along the longitudinal axis of the device from the upper surface of support member 16 constituting the bottom surface of well region 13a towards the upper surface U of support member 16 constituting the bottom surface of well region 14a thus forming a surface gradient. After the test biomolecules are immobilized on support member 16, the top member is placed onto support member 16 and a rigid frame with the standard microtiter footprint is placed around the outer perimeter of top member 11 and cells are added to well region 14a. In an alternative embodiment, after the test biomolecules are immobilized on support member 16 and the top member is placed over support member 16, a gel matrix is added to channel region 15a. Cells are subsequently added to well region 14a. The biological sample of cells potentially respond to the concentration gradient of immobilized biomolecules and migrates towards the higher concentrations of the test biomolecules, away from the higher concentrations of the test biomolecules, or exhibit inhibited migration in response to the higher concentrations of the test biomolecules. The surface gradient can increase linearly or as a squared, cubed, or logarithmic function or in any surface profile that can be approximated in steps up or down.

The test biomolecules can be attached to and form surface gradients on the upper surface U of support member 16 by various specific or non-specific approaches known in the art as described in K. Efimenko and J. Genzer, "How to Prepare Tunable Planar Molecular Chemical Gradient," 13 *Applied Materials,* 2001, No. 20, October 16; U.S. Pat. No. 5,514, incorporated herein by reference. For example, microcontact printing techniques, or any other method known in the art, can be used to immobilize on upper surface U of support member 16 a layer of SAMs presenting hexadecanethiol. Support member 16 is then exposed to high energy light through a photolithographic mask of the desired gradient micropattern or a grayscale mask with continuous gradations from white to black. When the mask is removed, a surface gradient of SAMs presenting hexandecanethiol remains. Support member 16 is then immersed in a solution of ethylene glycol terminated alkanethiol. The regions of support member 16 with SAMs presenting hexadecanethiol will rapidly adsorb biomolecules and the regions of the support member with SAMs presenting oligomers of the ethylene glycol group will resist adsorption of protein. Support member 16 is then immersed in a solution of the desired test biomolecules and the biomolecules rapidly adsorb only to the regions of support member 16 containing SAMs presenting hexadecanethiol creating a surface gradient of immobilized biomolecules.

In another embodiment, the test biomolecules are immobilized on the support member 16 and a surface concentration gradient forms after the top member 11 has been placed over support member 16 in any one of the embodiments of the test device of the present invention, such as the embodiments shown in FIGS. 1A–14. In this embodiment, discrete concentrations of solution containing test biomolecules are consecutively placed in well region 14a and allowed to adsorb non-specifically to support member 16. For example, first, a 1 milligram/milliliter (mg/ml) of solution can first be placed in well region 14a; second, a 1 microgram/milliliter ($\mu$g/ml) solution can be placed in well region 14a; last, a 1 nanogram/milliliter (ng/ml) solution of test biomolecules can be placed in well region 14a. The differing concentrations of test biomolecules in solution result in differing amounts of adsorption on support member 16.

Utilizing an alternative embodiment of device 10 containing an alternative design of chamber 12 as seen in FIG. 11, an immobilized biomolecular surface gradient is formed based on the concept of laminar flow of multiple parallel liquid streams, a method known in the art. Based on this concept, when two or more streams with low Reynolds numbers are joined into a single stream, also with a low Reynolds number, the combined streams flow parallel to each other without turbulent mixing. According to one embodiment, a solution of chemotactic biomolecules is placed in 17a and 19a and a protein solution is placed in 18a. The solutions are allowed to flow into channel region 15a under the influence of gentle aspiration at well region 14a. Biomolecules adsorb nonspecifically to the regions of the surface over which the solution containing the biomolecules flows forming a surface gradient. The wells are then filled with a suspension of cells and potential haptotaxis of the cells towards the increasing concentration gradient of biomolecules is observed and monitored. See generally, S. Takayama et al., "Patterning Cells and their Environment Using Multiple Laminar Fluid Flows in Capillary Networks" *Pro. Natl. Acad. Sci. USA,* Vol. 96, pp. 5545–5548, May 1999.

The present invention also contemplates an assay using both a soluble and surface gradient to determine whether the soluble test substance or the immobilized test biomolecules more heavily influence chemotaxis and chemoinvasion. In this embodiment, an assay is performed by forming a surface gradient as described above, an assay is performed by forming a solution gradient as described above, an assay is performed by forming both types of gradients and the results of all three assays are compared. With respect to the combined gradient assay, test biomolecules are immobilized on the upper surface U of support member 16 constituting the bottom surface of well region 13a and on the upper surface of support member 16 underlying channel region 15a and the concentration of biomolecules decreases along the longitudinal axis of chamber 12 from well region 13a to well region 14a, in any one of the embodiments of the test device of the present invention, such as the embodiments shown in FIGS. 1A–14. Additionally, a soluble test substance is added to well region 13a. Such an embodiment creates surface and soluble chemotactic concentration gradients that decrease in the same direction. If the combined concentration gradients have a synergistic effect on chemotaxis and/or chemoinvasion, then both gradients should be used in screening both the cell receptor binding the chemotactic ligands of the soluble chemotactic substance and the cell receptor binding the immobilized biomolecules. Both types of receptors are identified as important and therapeutic agents that target both these receptors or a combination of therapeutic agents, one targeting one receptor and another targeting the other receptor can be screened. If the combined concentration gradients do not have a synergistic effect, then the individual gradient that more strongly promotes chemotaxis and/or chemoinvasion can be identified and the cell receptor that binds to the chemotactic ligands of the test agent forming the gradient can be targeted.

Identifying optimal chemotactic ligand and receptor pairs is important in understanding the biological pathways implicated in chemotaxis and/or chemoinvasion and developing therapeutic agents that target these pathways. Accordingly, the present invention generally provides using chemotactic test agents to determine which chemotactic receptors expressed on a cell's surface most heavily influence chemotaxis and/or chemoinvasion. In one embodiment, the present invention provides for high throughput screening of a class of chemoattractants known to attract a particular cell type having a receptor on the cell's surface for each chemoattractant within this class in order to identify which receptor is more strongly implicated in the chemotaxis and/or chemoinvasion process. After identifying this receptor, the present invention contemplates high-throughput screening of therapeutic agents that potentially block this receptor or bind to this receptor, depending on whether chemotaxis and/or chemoinvasion is desired to be promoted or prevented. In another embodiment, the present invention provides for high throughput screening of different chemoattractants known to bind to the same receptor on a particular cell type's surface, in order to determine which chemoattractant ligand/receptor pair more heavily influences chemotaxis and/or chemoinvasion. After identifying this ligand/receptor pair, the present invention contemplates high throughput screening of therapeutic agents that target this receptor and either block or activate this receptor depending one whether chemotaxis and/or chemoinvasion is desired to be promoted or prevented.

The present invention also contemplates high-throughput screening of a class of chemotactic inhibitors known to inhibit chemotaxis of a particular cell type having various chemotactic receptors on the cell's surface in order identify which receptor is more strongly implicated in the chemotaxis and chemoinvasion process. After identifying this receptor, the present invention provides for high throughput screening of therapeutic agents that potentially block this receptor as well (if such action is desired).

In one embodiment of the present invention, an assay is performed to determine whether a test compound inhibits cancer cell invasion. In this embodiment, untreated cancer cells are placed in well region 14a and a test agent is placed in well region 13a of chamber 12 in any one of the embodiments of the test device of the present invention, such as the embodiments shown in FIGS. 1A–14. Cell chemotaxis and invasion is measured and recorded. After a suitable test agent is identified (one that chemically attracts the cancer cells) another assay is run in chamber 12. In this subsequent assay, cancer cells are placed in well region 14a and a test compound, for example, a therapeutic, is also placed in well region 14a. In another embodiment, the test compound is also placed in channel region 15a. If a gel matrix is to be added to channel region 15a, the test compound can be mixed with the gel matrix before the gel is contacted with channel region 15a during fabrication of device 10. A subsequent sample of the test agent identified in the first assay is placed in well region 13a and the chemotaxis and invasion of the cells treated with the test compound is compared to the chemotaxis and invasion of the cells not treated with the test compound. The test compound's anti-cancer potential is measured by whether the treated cancer cells have a slower chemotaxis and invasion rate than the untreated cancer cells.

With respect to another exemplary use of the chemotaxis and chemoinvasion device of the present invention, the device can be used to assay cells' response to the inflammatory response. A local infection or injury in any tissue of the body attracts leukocytes into the damaged tissue as part of the inflammatory response. The inflammatory response is mediated by a variety of signaling molecules produced within the damaged tissue site by mast cells, platelets, nerve endings and leukocytes. Some of these mediators act on capillary endothelial cells, causing them to loosen their attachments to their neighboring endothelial cells so that the capillary becomes more permeable. The endothelial cells are also stimulated to express cell-surface molecules that recognize specific carbohydrates that are present on the surface of leukocytes in the blood and cause these leukocytes to adhere to the endothelial cells. Other mediators released from the damaged tissue act as chemoattractants, causing the bound leukocytes to migrate between the capillary endothelial cells into the damaged tissue. To study leukocyte chemotaxis, in one embodiment, channel region 15a is treated to simulate conditions in a human blood capillary during the inflammatory response. For example, the side walls of channel region 15a are coated with endothelial cells expressing cell surface molecules such as selecting, for example as shown in FIG. 4B. Leukocytes are then added to well region 14a and a known chemoattractant is added to well region 13a in any one of the embodiments of the test device of the present invention, such as the embodiments shown in FIGS. 1A–14. Other suitable cell types that can be added to well region 14a are neutrophils, monocytes, T and B lymphocytes, macrophages or other cell types involved in response to injury or inflammation. The leukocytes' chemotaxis across channel region 15a towards well region 13a is observed. Depending on the type of infection to be studied, different categories of leukocytes can be used. For example, in one embodiment studying cell chemotaxis in response to a bacterial infection, well region 14a receives neutrophils. In another embodiment studying cell chemotaxis in response to a viral infection, well region 14a receives T-cells. In another embodiment simulating the process of angiogenesis, it is known in the art that growth factors applied to the cornea induce the growth of new blood vessels from the rim of highly vascularized tissue surrounding the cornea towards the sparsely vascularized center of the cornea. Therefore in another exemplary assay utilizing the chemotaxis and chemoinvasion device, cells from corneal tissue are placed in well region 13a and endothelial cells are placed in well region 14a in any one of the embodiments of the test device of the present invention, such as the embodiments shown in FIGS. 1A–14. A growth factor is added to well region 13a and chemotaxis of the endothelial cells is observed, measured and recorded. Alternatively, since angiogenesis is also important in tumor growth (in order to supply oxygen and nutrients to the tumor mass), instead of adding growth factor to well region 13a, cancer cells from corneal tissue that produce angiogenic factors such as vascular endothelial growth factor (VEGF) could be added to well region 13a and normal endothelial cells added to well region 14a. In a different embodiment also related to the study of angiogenesis, mast cells, macrophages, and fat cells that release fibroblast growth factor during tissue repair, inflammation, and tissue growth are placed in well region 13a and endothelial cells are placed in well region 14a. Since during angiogenesis, a capillary sprout grows into surrounding connective tissue, to further simulate conditions in vivo, channel region 15a can be filled with a gel matrix.

There are several variations and embodiments of the aforementioned assays. One embodiment involves the number of channels connecting well region 13a and well region 14a of chamber 12 of device 10. In one embodiment, such as the ones shown in FIGS. 3A–3C, there are multiple channels connecting well region 13a to well region 14a. By using multiple channels, multiple assays can be performed simultaneously using one biological sample of cells. In such an embodiment, all assays are performed under uniform and consistent conditions and therefore provide statistically more accurate results. For example, each assay begins with exactly the same number of potentially migratory cells and exactly the same concentration of test agent. Once a concentration gradient forms, each assay is exposed to the gradient for the same period of time. These multiple channels also provide redundancy in case of failure in the assay.

Another embodiment of the cell invasion and chemotaxis assay of the present invention involves the placement of cells in well region 14a of chamber 12 in any one of the embodiments of the test device of the present invention, such as the embodiments shown in FIGS. 1A–14. The cells may be patterned in a specific array on the upper surface U of support member 16 constituting the bottom surface of well region 14a or may simply be deposited in no specific pattern or arrangement in well region 14a. If the cells are patterned in a specific array on the upper surface of support member 16 constituting the bottom surface of well region 14a, then preferably, during the fabrication of device 10, the upper surface of support member 16 constituting the bottom surface of well region 14a is first patterned with cells and then top member 11 is placed over support member 16. It is desirable to monitor cellular movement from a predetermined "starting" position to accurately measure the distance and time periods the cells travel. As such, in one embodiment, the cells are immobilized or patterned upon the support member underlying the first well in such a manner that the cells' viability is maintained and their position is definable so that chemotaxis and invasion may be observed. There are several techniques known in the art to immobilize and pattern the cells into discreet arrays onto the support member. A preferred technique is described in copending application Ser. No. 60/330,456. In one embodiment, a cell position patterning member is used to pattern the cells into definable areas onto the upper surface U of support member 16 constituting the bottom surface of well region 14a of top member 11. If, for example, top member 11 is fabricated in the footprint of a standard 96-well microtiter plate such that wells 13 and 14 correspond to the size and shape of the macrowells of the microtiter plate (not shown), then the cell position pattern member has outlined areas which correspond to the size and shape of wells 13 and 14 and therefore correspond to the size and shape of the macrowells of the microtiter plate. Each outlined area has micro through holes through which the cells will be patterned. In order to pattern the cells, the cell position patterning member iscontacted with support member 16 and the outlined areas of the cell position patterning member are aligned with portion of upper surface U of support member 16 that constitutes the bottom surface of well region 14a, and will ultimately correspond to well region 14a once top member 11 is contacted with support member 16. Cells are then deposited over the cell position patterning member and filter through the micro through holes of the patterning member onto the support member underlying the areas corresponding to through-holes corresponding to second well regions 14a of chambers 12. Top member 11 is then placed over support member 16 such that through-holes 14a are placed over the area of support member 16 in which the cells are patterned. These patterning steps result in discrete arrays of cells in well region 14a.

Preferably, the cell position patterning member comprises an elastomeric material such as PDMS. Using PDMS for the patterning member provides a substantially fluid-tight seal between the patterning member and the support member. This substantially fluid-tight seal is preferable between these two components because cells placed in the wells are less likely to infiltrate adjoining wells if such a seal exists between the patterning member and the support member. The arrangement of the micro through holes of the patterning member may be rectangular, hexagonal, or another array resulting in the cells being patterned in these respective shapes. The width of each micro-through hole may be varied according to cell types and desired number of cells to be patterned. For example, if the width of both cell and micro through hole is 10 microns, only one cell will deposit through each micro through hole. Thus, in this example, if the width of micro through hole is 100 microns up to approximately 100 cells may be deposited.

The present invention also contemplates the patterning of more than one cell type on the upper surface of support member 16 constituting the bottom surface of well region 14a in any one of the embodiments of the test device of the present invention, such as the embodiments shown in FIGS. 1A–14. Since cells of one type in vivo rarely exist in isolation and are instead in contact and communication with other cell types, it is desirable to have a system in which cells can be assayed in an environment more like that of the body. For example, since cancer cells are never found in isolation, but rather surrounded by normal cells, an assay designed to test the effect of a drug on cancer cells would be more accurate if the cancer cells in the assay were surrounded by normal cells. In testing an anti-cancer drug, cancer cells may be patterned on the upper surface of support member 16 constituting the bottom surface of well region 14a in any given one of the embodiments of the test device of the present invention, such as the embodiments of FIGS. 1A–14, and then through a separate patterning procedure, the cancer cells may be surrounded by stromal cells. To pattern two different cell types on the upper surface of support member 16 constituting the bottom surface of well region 14a, a micro cell position patterning member, as described above, is contacted with support member 16 and the outlined areas of the cell position patterning member are aligned with the portion of upper surface U of support member 16 that constitutes the bottom surface of well region 14a, and will ultimately correspond to well region 14a once top member 11 is contacted with support member 16. Cells of a first type may then be deposited over the cell position patterning member and filter through the micro through holes of the patterning member onto the portion of the upper surface U of support member 16 constituting the bottom surface of well region 14a. The micro cell position patterning member may then be removed from support member 16. A macro cell position patterning member with outlined areas that correspond to the size and shape of wells 13 and 14 and may therefore correspond to the size and shape of the macrowells of a 96 well microtiter plate. The macro cell position patterning member has macro through holes. A macro through hole of the macro cell position patterning member encompasses an area larger than the surface area defined by a micro through hole of the micro cell position patterning member, but smaller than the surface area defined by well region 14a of chamber 12. The macro cell position patterning member may then be contacted with support member 16. Cells of a second type may then be deposited over the macro cell position patterning member and filter through the macro through holes of the macro cell position patterning member onto the portion of upper surface U of support member 16 constituting the bottom surface of well regions 14a once top member 11 is contacted with support member 16. Such patterning arrangement may result in cells of a second type surrounding and "stacking" cells of a first type. If it is desired to only have the cells of the second type stack the cells of the first type, then the same micro cell position patterning member used to deposit the first cell type or a different micro cell position patterning member having the exact same configuration as the patterning member used to deposit cells of a first type, may be used to deposit cells of a second type. After the cells are patterned on support member 16, top member 11 may be contacted with support member 16 such that through holes in top member 11 corresponding to the well region 14a encompass the areas patterned with cells. This essentially results in cells being immobilized in a specific array within well region 14a.

Notwithstanding how many different cell types are patterned on the upper surface of support member 16 constituting the bottom surface of well region 14a, the cells may be patterned on the support member through several methods known in the art. For example, the cells may be patterned on support member 16 through the use of SAMS. There are several techniques known in the art to pattern cells through the use of SAMs of which a few exemplary techniques disclosed in U.S. Pat. No. 5,512,131 to Kumar et al., U.S. Pat. No. 5,620,850 to Bambad et al., U.S. Pat. No. 5,721,131 to Rudolph et al., U.S. Pat. Nos. 5,776,748 and 5,976,826 to Singhvi et al. are incorporated by reference herein.

Several methods are known in the art to tag the cells in order to observe and measure the aforementioned parameters. In one embodiment, an unpurified sample containing a cell type of interest is incubated with a staining agent that is differentially absorbed by the various cell types. The cells are then placed in well region 14a of chamber 12 in any given one of the embodiments of the test device of the present invention, such as the embodiments of FIGS. 1A–14. Individual, stained cells are then detected based upon color or intensity contrast, using any suitable microscopy technique(s), and such cells are assigned positional coordinates. In another embodiment, an unpurified cell sample is incubated with one or more detectable reporters, each reporter capable of selectively binding to a specific cell type of interest and imparting a characteristic fluorescence to all labeled cells. The sample is then placed in well region 14a of chamber 12 in any given one of the embodiments of the test device of the present invention, such as the embodiments of FIGS. 1A–14. The sample is then irradiated with the appropriate wavelength light and fluorescing cells are detected and assigned positional coordinates. One skilled in the art will recognize that a variety of methods for discriminating selected cells from other components in an unpurified sample are available. For example, these methods can include dyes, radioisotopes, fluorescers, chemiluminescers, beads, enzymes, and antibodies. Specific labeling of cell types can be accomplished, for example, utilizing fluorescently-labeled antibodies. The process of labeling cells is well known in the art as is the variety of fluorescent dyes that may be used for labeling particular cell types.

Cells of a chosen type may be also differentiated in a mixed-cell population, for example, using a detectable reporter or a selected combination of detectable reporters that selectively and/or preferentially bind to such cells. Labeling may be accomplished, for example, using monoclonal antibodies that bind selectively to expressed CDs, antigens, receptors, and the like. Examples of tumor cell antigens include CD13 and CD33 present on myeloid cells; CD10 and CD19 present on B-cells; and CD2, CD5, and CD7 present on T-cells. One of skill in the art will recognize that numerous markers are available that identify various known cell markers. Moreover, additional markers are continually being discovered. Any such markers, whether known now or discovered in the future, that are useful in labeling cells may be exploited in practicing the invention.

Since few, if any markers are absolutely specific to only a single type of cell, it may be desirable to label at least two markers, each with a different label, for each chosen cell type. Detection of multiple labels for each chosen cell type should help to ensure that the chemotaxis and chemoinvasion analysis is limited only to the cells of interest.

The present invention further provides a test device comprising: support means; means mounted to the support means for defining a discrete chamber with the support means by being placed in fluid-tight, conformal contact with the support means. The discrete chamber includes a first well region including at least one first well; a second well region including at least one second well, the second well region further being horizontally offset with respect to the first well region in a test orientation of the device; and a channel region including at least one channel connecting the first well region and the second well region with one another. An example of the support means comprises the support member 16 shown in FIGS. 1A, 1B, 12 and 13, while an example of the means mounted to the support means comprises the top member 11 shown in FIGS. 1A–11, 13 and 14. Other such means would be well known by persons skilled in the art.

From the foregoing, it will be observed that numerous modifications and variations can be effected without departing from the true spirit and scope of the novel concept of the present invention. For example, different embodiments of a device of the present invention may be combined. Embodiments of the present invention further contemplate different types of assays, for example, an assay wherein the test agent comprises a buffer solution instead of a chemotactic agent. In such an assay, cell migration through channel region 15a in observed in the absence of a chemotactic gradient.

It will be appreciated that the present disclosure is intended to set forth the exemplifications of the invention, and the exemplifications set forth are not intended to limit the invention to the specific embodiments illustrated. The disclosure is intended to cover by the appended claims all such modifications as fall within the spirit and scope of the claims.

EXAMPLES

Example 1

Procedure for Fabrication of Chemoinvasion Device

A silicon wafer (6 inches) is spin coated with photoresist (SU8-50) at 2000 rpm for 45 seconds. After baking the wafer on a hot plate at 115° C. for 10 minutes, the wafer is allowed to cool to room temperature. A mask aligner (EVG620) is used to expose the photoresist film through a photomask. Exposure of 45 seconds is followed by another hard bake at 115° C. for 10 minutes. The silicon wafer is allowed to cool to room temperature for over 30 minutes. The uncrosslinked photoresist is removed using propylene glycol methyl ether acetate (PGMEA). The wafer is dried under a stream of nitrogen, and the patterned photoresist is ready for subsequent processing.

In one embodiment, the patterned photoresist is spin-coated with another layer of SU8-100 at 1500 rpm for 45 seconds. A mask aligner is used to selectively expose macrofeatures (i.e. wells) of the top member but not expose channel regions connecting the wells and other areas of the top member. After post exposure processing and photoresist removal, the master contains multiple layered features. This step may be repeated to introduce macro-features on the master, which have the height of approximately 3 mm.

When a PDMS prepolymer is cast against the master, it faithfully replicates the features in the master. When casting, PDMS is added in an amount slightly lower than the height of the macrofeatures. After curing the PDMS for four hours at 65 degrees C., the PDMS is peeled off the silicon master and thoroughly cleaned with soap and water and rinsed with 100% ethanol. A glass support member is also cleaned and rinsed with ethanol. The PDMS membrane and glass support member are plasma oxidized for 1 minute with the sides that would be bonded together facing upward. The PDMS membrane is then placed onto the glass support member and pressure is applied to remove any air bubbles that may have formed between the PDMS membrane and the glass support member. The assembled device is then cooled to 4° C. Within 15 minutes of the plasma oxidation of the PDMS membrane and the glass support member, 20 microliters ($\mu$l) of Matrigel (any other hydrogel may be used) is poured into the first well and allowed to flow into the capillaries. The device is placed at room temperature for 15 minutes to set the Matrigel. Excess gel is then removed from the wells of the top member using a vacuum and a Pasteur pipette.

Example 2

Cell Chemoinvasion Assay
Placement of Cells and Test Agent in Chamber

The first and second wells of a chamber of a top member are filled with phosphate buffered saline solution, PBS. The bottom of the second well may be treated with fibronectin (1 mg/ml) or other extracellular matrix protein for 30 minutes, followed by washing twice with PBS. After aspirating PBS, astrocytoma cells (U87-MG) are plated in 50 $\mu$l of freshly warmed medium in the second well (25,000 cells per well of a 24-well plate, in volume of 50 ul of solution per well). The cells deposit through the second well of the chamber, and attach to the bottom of the second well.

Cells are left to attach and spread in the second well overnight in a 37° C. incubator. At the start of the experiment, the cell medium is exchanged for fresh serum-free medium. 10 $\mu$g of bFGF (basic fibroblast growth factor) per ml of medium is added to the first well of each chamber.

Image Acquisition and Data Analysis

Digital Images are taken on a Zeiss inverted microscope using AXIOCAM™. Data was analyzed on AXIOVISION™ software. Time-lapsed images are taken every day at the same time for four days.

Example 3

Cell Chemoinvasion Inhibition Assay Using Solution Gradient

Placement of Cells and Test Agent in Chambers

With respect to three chambers, the wells of each chamber of a top member are filled with PBS. The bottom of the second wells may be treated with fibronectin (1 mg/ml) or other extracellular matrix protein for 30 minutes, followed by washing twice with PBS. After aspirating PBS, U87-MG cells are plated in 50 $\mu$l of freshly warmed medium in the second wells (10,000 cells per well of a 24-well plate, in volume of 50 $\mu$l of medium per well). The cells deposit through the second wells of each chamber, and adhere to the bottom of the second wells.

Cells are left to attach and spread in the second wells overnight in a 37° C. incubator. At the start of the experiment, the cell medium is exchanged for fresh serum-free medium or 1% serum. 1 $\mu$g of bFGF (basic fibroblast growth factor) per ml of medium is added to the first wells of the chamber. A solution gradient is allowed to form for one hour.

With respect to the three different chambers, 100 $\mu$M of LY294002 are placed in the second well of chamber #1, 10 $\mu$M LY294002 of are placed in the second well of chamber #2, and 1.0 $\mu$M of LY294002 are placed in the second well of chamber #3.

Image Acquisition and Data Analysis

Digital Images are taken on a Zeiss inverted microscope using AXIOCAM™. Data was analyzed on AXIOVISION™ software. Time-lapsed images are taken every day at the same time for four days.

Example 4

Immobilization of Biomolecules on Support Member

After assembling the device as described above, the channel regions are filled with ethanolic solution containing $(CH_3CH_2O)_3Si\ (CH_2)_3NH_2$. After 20 minutes at room temperature, the channel regions are washed off using ethanol. The device is incubated at 105° C. for one hour to crosslink the siloxane monolayer formed on the support member. The device is washed with ethanol to remove residues. The channel regions are filled with a solution of diisocyanate, either hexamethylene diisocyanate or tolyl diisocyanate (1% in acetonitrile or N-methyl pyrrolidinone). The diisocyanate is allowed to react for two hours with the terminal amino groups of the siloxane monolayer formed on the support member. The diisocyanate is washed off. The channel regions are filled with 1 mg/ml solution of heparan sulfate or other sulfated carbohydrates (for example, di-acetylated form of heparin, heparin fragments, lectins containing sulfated sugars, etc.) The heparan sulfate is allowed to react with the support member to form immobilized species. The heparan sulfate solution and other reagents are washed off. A chemokine solution (any chemokine from CC, CXC, CX3C, or XC families may be used) is introduced into the channel region. By electrostatic interaction, chemokines that have higher pI (~9–10) adsorb onto the negatively charged sulfated support member.

Example 5

Chemotaxis Inhibition Assay Using Surface Gradient

Two wells are filled with 50 $\mu$l of PBS, and hydrostatic pressure is allowed to equalize. 5 $\mu$l of anti-hisx6 antibody are added to the first well and 5 $\mu$l of buffer are added to the second well to equalize hydrostatic pressure. By diffusion, the antibody concentration forms a gradient from the first well to the second well. After 2 hours at room temperature, the two wells are washed off by adding 50 $\mu$l of buffer to the second well and removing 50 $\mu$l from the first well. By physisorption, the solution gradient is transferred onto a surface thereby forming a surface gradient. A solution of IL-8 (recombinant human IL-8 with a HIS×6 fusion tag, R+D systems, catalog No. 968-IL) at concentration of 25 $\mu$g/ml is added to the channel regions. The solution is allowed to incubate for 30 minutes at room temperature. Excess IL-8 chemokine is washed off and the surface is decorated with bound IL-8. Neutrophils(freshly isolated from a healthy donor) are added to the second well. Typically 20,000–100,000 cells are added in volume ranging from 10–550 $\mu$l. Neutrophils are allowed to adhere to the support member and allowed to migrate towards the higher concentration of IL-8. Inhibition of migration is achieved by adding polyclonal antibody against IL-8.

What is claimed is:

1. A method of monitoring haptotaxis comprising:
   providing a device for monitoring haptotaxis having a housing defining a chamber, the chamber including:
   a first well region including at least one first well, the first well region configured to receive immobilized test biomolecules therein and further including test biomolecules immobilized therein;
   a second well region including at least one second well, the second well region configured to receive a sample comprising cells therein and further being horizontally offset with respect to the first well region in a test orientation of the device; and
   a channel region with test biomolecules immobilized therein and including at least one channel connecting the first well region and the second well region with one another.
   forming a surface concentration gradient along a longitudinal axis of the chamber by decreasing the concentration of test biomolecules from the at least one first well to the at least one second well;
   placing a first sample comprising cells in the at least one second well; and
   monitoring haptotaxis of the cells.

2. The method of claim 1, wherein the chamber comprises a plurality of chambers.

3. The method of claim 2, wherein each of the first well region and the second well region of the plurality of chambers are disposed relative to one another to match a pitch of a standard microtiter plate.

4. The method of claim 2, wherein the plurality of chambers is disposed relative to one another to match a pitch of a standard microtiter plate.

5. The method of claim 1, wherein the at least one channel comprises a plurality of channels.

6. The method of claim 1, wherein the housing comprises a support member and a top member, the top member being in reversible, fluid tight conformal contact with the support member, the top member and the support member configured such that they together define the chamber.

7. The method of claim 1, wherein a soluble test substance is added to the at least one first well to form a solution concentration gradient along the longitudinal axis of the chamber.

8. The method of claim 7, wherein the soluble test substance is a chemoattractant, chemorepellant, or chemotactic inhibitor.

9. The method of claim 1, wherein the test biomolecules are chemoattractants, chemorepellants, or chemotactic inhibitors.

10. The method of claim 1, wherein the test biomolecules are chemokines, cytokines, or small molecules.

11. The method of claim 1, further comprising adding a test compound to the at least one second well.

12. The method of claim 11, wherein the test compound is a therapeutic agent, a chemotactic inhibitor, a chemoattractant, or a chemorepellant.

13. The method of claim 1, wherein the test biomolecules are immobilized in the first well region and the channel region through the use of self-assembled monolayers.

14. The method of claim 1, wherein placing the first sample comprising cells in the at least second well comprises patterning the cells in discrete arrays.

15. The method of claim 1, further comprising placing a second sample comprising cells in the at least one second well.

* * * * *